US009447037B2

(12) United States Patent
Sinha et al.

(10) Patent No.: US 9,447,037 B2
(45) Date of Patent: Sep. 20, 2016

(54) 4-(5-(4-CHLOROPHENYL)-2-(2-CYCLOPROPYLACETYL)-1,4-DIMETHYL-1H-PYRROL-3-YL)BENZENESULFONAMIDE AS ALPHA 7 NACHR MODULATOR (71) Applicant: Lupin Limited, Mumbai, Maharashtra (IN)

(72) Inventors: Neelima Sinha, Pune (IN); Navnath Popat Karche, Pune (IN); Ajay Ramchandra Tilekar, Pune (IN); Venkata P. Palle, Pune (IN); Rajender Kumar Kamboj, Pune (IN)

(73) Assignee: Lupin Limited, Mumbai (IN)

( * ) Notice: Subject to any disclaimer, the term of this patent is extended or adjusted under 35 U.S.C. 154(b) by 0 days.

(21) Appl. No.: 14/894,803

(22) PCT Filed: Jun. 2, 2014

(86) PCT No.: PCT/IB2014/061891
§ 371 (c)(1),
(2) Date: Nov. 30, 2015

(87) PCT Pub. No.: WO2014/195848
PCT Pub. Date: Dec. 11, 2014

(65) Prior Publication Data
US 2016/0107990 A1  Apr. 21, 2016

(30) Foreign Application Priority Data
Jun. 3, 2013  (IN) .......................... 1937/MUM/2013

(51) Int. Cl.
C07D 207/335 (2006.01)
C07D 207/333 (2006.01)
A61K 31/40 (2006.01)
A61K 45/06 (2006.01)

(52) U.S. Cl.
CPC ........... *C07D 207/335* (2013.01); *A61K 31/40* (2013.01); *A61K 45/06* (2013.01); *C07D 207/333* (2013.01)

(58) Field of Classification Search
CPC ................................................ C07D 207/335
See application file for complete search history.

(56) References Cited

U.S. PATENT DOCUMENTS

| 7,683,084 B2 | 3/2010 | Faghih et al. |
| 7,741,364 B2 | 6/2010 | Faghih et al. |
| 2006/0142349 A1 | 6/2006 | Hurst et al. |
| 2007/0142450 A1 | 6/2007 | Dahl et al. |
| 2009/0253691 A1 | 10/2009 | Thuring et al. |
| 2010/0190819 A1 | 7/2010 | Kanner |
| 2010/0222398 A1 | 9/2010 | Nardi et al. |
| 2010/0227869 A1 | 9/2010 | Peters et al. |
| 2010/0240707 A1 | 9/2010 | Thuring et al. |
| 2015/0231143 A1 | 8/2015 | Sinha et al. |
| 2015/0291617 A1 | 10/2015 | Sinha et al. |
| 2015/0299178 A1 | 10/2015 | Sinha et al. |
| 2015/0344422 A1 | 12/2015 | Sinha et al. |

FOREIGN PATENT DOCUMENTS

| EP | 1866314 B1 | 9/2010 | |
| IN | WO 2012114285 A9 * | 10/2012 | ......... C07D 207/333 |
| WO | WO 2007/031440 A2 | 3/2007 | |
| WO | WO 2009/043780 A1 | 4/2009 | |
| WO | WO 2009/043784 A1 | 4/2009 | |
| WO | WO 2009/115547 A1 | 9/2009 | |
| WO | WO 2009/127678 A1 | 10/2009 | |
| WO | WO 2009/127679 A1 | 10/2009 | |
| WO | WO 2009/135944 A1 | 11/2009 | |
| WO | WO 2009/145996 A2 | 12/2009 | |
| WO | WO 2010/130768 A1 | 11/2010 | |
| WO | WO 2011/036167 A1 | 3/2011 | |
| WO | WO 2011/064288 A1 | 6/2011 | |
| WO | WO 2012/104782 A1 | 8/2012 | |
| WO | WO 2012/114285 A9 | 8/2012 | |
| WO | WO 2012/131576 A1 | 10/2012 | |
| WO | WO 2013/005153 A1 | 1/2013 | |
| WO | WO 2013/132380 A1 | 9/2013 | |
| WO | WO 2014/111839 A1 | 7/2014 | |

OTHER PUBLICATIONS

International Search Report in corresponding International Application No. PCT/IB2014/061891, mailed Aug. 28, 2014.
Albuquerque, E.X., et al., "Modulation of Nicotinic Receptor Activity in the Central Nervous System: A Novel Approach to the Treatment of Alzheimer Disease," *Alzheimer Disease and Associated Disorders*, vol. 15, Suppl. 1, pp. S19-S25 (2001).
Alkondon, Manickavasagom, et al., "α7 Nicotinic acetylcholine receptors and modulation of gabaergic synaptic transmission in the hippocampus," *European Journal of Pharmacology*, vol. 393, pp. 59-67 (2000).
Arias, Hugo R., et al., "Role of non-neuronal nicotinic acetylcholine receptors in angiogenesis," *The International Journal of Biochemistry & Cell Biology*, vol. 41, pp. 1441-1451 (2009).
Barder, Timothy E., et al., "Catalysts for Suzuki-Miyaura Coupling Processes: Scope and Studies of the Effect of Ligand Structure," *Journal of the American Chemical Society*, vol. 127, pp. 4685-4696 (2005).
Berge, Stephen M., et al., "Pharmaceutical Salts," Review Article from *Journal of Pharmaceutical Sciences*, vol. 66, No. 1, pp. 1-19 (Jan. 1977).
Bitner, Robert S., et al., "Broad-Spectrum Efficacy across Cognitive Domains by α7 Nicotinic Acetylcholine Receptor Agonism Correlates with Activation of ERK1/2 and CREB Phosphorylation Pathways," *The Journal of Neuroscience*, vol. 27, No. 39, pp. 10578-10587 (Sep. 26, 2007).

(Continued)

Primary Examiner — Matthew Coughlin
(74) Attorney, Agent, or Firm — Leydig, Voit & Mayer, Ltd.

(57) ABSTRACT

Disclosed are an alpha 7 nAChR receptor modulator compound, 4-(5-(4-chlorophenyl)-2-(2-cyclopropylacetyl)-1,4-dimethyl-1H-pyrrol-3-yl)benzenesulfonamide, its tautomeric form, its pharmaceutically acceptable salts, pharmaceutical compositions comprising the compound or a salt thereof, and a method of treating various diseases, disorders or conditions, for example, Alzheimer's disease, mild cognitive impairment, senile dementia, vascular dementia, dementia of Parkinson's disease, and attention deficit disorder.

6 Claims, 2 Drawing Sheets (56) References Cited

OTHER PUBLICATIONS

Boess, Frank G., et al., "The Novel α7 Nicotinic Acetylcholine Receptor Agonist N-[(3R)-1-Azabicyclo[2.2.2]oct-3-yl]-7-[2-(methoxy)phenyl]-1-benzofuran-2-carboxamide Improves Working and Recognition Memory in Rodents," *The Journal of Pharmacology and Experimental Therapeutics*, vol. 321, No. 2, pp. 716-725 (2007).

Bruchfeld, A., et al., "Whole blood cytokine attenuation by cholinergic agonists ex vivo and relationship to vagus nerve activity in rheumatoid arthritis," *Journal of Internal Medicine*, vol. 268, No. 1, pp. 94-101 (Jul. 2010).

Calleja-Macias, Itzel E., "Cholinergic signaling through nicotinic acetylcholine receptors stimulates the proliferation of cervical cancer cells: An explanation for the molecular role of tobacco smoking in cervical carcinogenesis?," *International Journal of Cancer*, vol. 124, pp. 1090-1096 (2009).

Cannon, Tyrone D., "The inheritance of intermediate phenotypes for schizophrenia," *Current Opinion in Psychiatry*, vol. 18, pp. 135-140 (2005).

Carson, Robyn, et al., "Genetic Variation in the α7 Nicotinic Acetylcholine Receptor is Associated with Delusional Symptoms in Alzheimers's Disease," *NeuroMolecular Medicine*, vol. 10, pp. 377-384 (2008).

Chan, Wai Kit, et al., "Frontal cortical α7 and α4β2 nicotinic acetylcholine receptors in working and reference memory," *Neuropharmacology*, vol. 52, pp. 1641-1649 (2007).

Clark, Robert E., et al., "Impaired Recognition Memory in Rats after Damage to the Hippocampus," *The Journal of Neuroscience*, vol. 20, No. 23, pp. 8853-8860 (Dec. 1, 2000).

Curzon, Peter, et al., "Antisense knockdown of the rat α7 nicotinic acetylcholine receptor produces spatial memory impairment," *Neuroscience Letters*, vol. 410, pp. 15-19 (2006).

Dajas-Bailador, Federico, et al., "Nicotinic acetylcholine receptors and the regulation of neuronal signalling," *Trends in Pharmacological Sciences*, vol. 25, No. 6, pp. 317-324 (Jun. 2004).

Damaj, M. Imad, et al., "The antinociceptive effects of α7 nicotinic agonists in an acute pain model," *Neuropharmacology*, vol. 39, pp. 2785-2791 (2000).

Dantzer, Robert, et al., "Cerebral lateralization of olfactory-mediated affective processes in rats," *Behavioural Brain Research*, vol. 40, pp. 53-60 (1990).

Decker, Michael W., et al., "The therapeutic potential of nicotinic acetylcholine receptor agonists for pain control," *Expert Opinion on Investigational Drugs*, vol. 10, No. 10, pp. 1819-1830 (2001).

Deluca, Patrick P., et al., "Parenteral Drug-Delivery Systems," *Pharmaceutics and Pharmacy Practice*, Chapter 8, J.B. Lippincott Company, Philadelphia, PA, pp. 238-250 (1982).

Deutsch, Stephen I., et al., "Progressive Worsening of Adaptive Functions in Down Syndrome May Be Mediated by Complexing of Soluble Aβ Peptides With the $α_7$ Nicotinic Acetylcholine Receptor: Therapeutic Implications," *Clinical Neuropharmacology*, vol. 26, No. 5, pp. 277-283 (2003).

Dickerson, Faith, et al., "Neurocognitive deficits and social functioning in outpatients with schizophrenia," *Schizophrenia Research*, vol. 21, pp. 75-83 (1996).

Donnelly-Roberts, Diana L., et al., "ABT-594 [(R)-5-(2-Azetidinylmethoxy)-2-Chloropyridine]: A Novel, Orally Effective Analgesic Acting via Neuronal Nicotinic Acetylcholine Receptors: I. In Vitro Characterization," *The Journal of Pharmacology and Experimental Therapeutics*, vol. 285, No. 2, pp. 777-786 (1998).

Dunlop, John, et al., "Old and New Pharmacology: Positive Allosteric Modulation of the α7 Nicotinic Acetylcholine Receptor by the 5-Hydroxytryptamine$_{2B/C}$ Receptor Antagonist SB-206553 (3,5-Dihydro-5-methyl-N-3-pyridinylbenzo[1,2-b:4,5-b'] di pyrrole-1-(2H)-carboxamide)," *The Journal of Pharmacology and Experimental Therapeutics*, vol. 328, No. 3, pp. 766-776 (2009).

Duris, Kamil, et al, "α7 Nicotinic Acetylcholine Receptor Agonist PNU-282987 Attenuates Early Brain Injury in a Perforation Model of Subarachnoid Hemorrhage in Rats," *Stroke*, vol. 42, pp. 3530-3536 (2011).

Dvornikova, Elena, et al., "Synthesis of 2- and 3-Substituted N-Methylpyrroles," *Synlett*, vol. 7, pp. 1152-1153 (2002).

Ebbert, Jon O., et al., "Varenicline for smoking cessation: efficacy, safety, and treatment recommendations," *Patient Preference and Adherence*, vol. 4, pp. 355-362 (2010).

Ennaceur, A., "One-trial object recognition in rats and mice: Methodological and theoretical issues," *Behavioural Brain Research*, vol. 215, pp. 244-254 (2010).

EnVivo Pharmaceuticals, "EnVivo Reports Positive Results of Its EVP-6124 Clinical Bio-Marker Study in Schizophrenia Patients," Press Release (Jan. 12, 2009).

Faghih, Ramin, et al., "Discovery of 4-(5-(4-Chlorophenyl)-2-methyl-3-propionyl-1H-pyrrol-1-yl)benzenesulfonamide (A-867744) as a Novel Positive Allosteric Modulator of the α7 Nicotinic Acetylcholine Receptor," *Journal of Medicinal Chemistry*, vol. 52, pp. 3377-3384 (2009).

Fehér, Ágnes, et al., "Association between a Genetic Variant of the Alpha-7 Nicotinic Acetylcholine Receptor Subunit and Four Types of Dementia," *Dementia and Geriatric Cognitive Disorders*, vol. 28, pp. 56-62 (2009).

Freedman, Robert, et al., "Evidence in Postmortem Brain Tissue for Decreased Numbers of Hippocampal Nicotinic Receptors in Schizophrenia," *Biological Psychiatry*, vol. 38, pp. 22-33 (1995).

Freedman, Robert, et al., "The Genetics of Sensory Gating Deficits in Schizophrenia," *Current Psychiatry Reports*, vol. 5, pp. 155-161 (2003).

Gallowitsch-Puerta, Margot, et al., "Neuro-immune interactions via the cholinergic anti-inflammatory pathway," *Life Sciences*, vol. 80, No. 24-25, pp. 2325-2329 (May 30, 2007).

Giebelen, Ida A., et al., "Stimulation of α7 Cholinergic Receptors Inhibits Lipopolysaccharide-Induced Neutrophil Recruitment by a Tumor Necrosis Factor α-Independent Mechanism," *Shock*, vol. 27, No. 4, pp. 443-447 (2007).

Goldstein, Richard, et al., "Cholinergic Agonists Inhibit LPS Induced Whole Blood TNF Release Ex Vivo in Patients With Severe Sepsis: A Pilot Study," *Academic Emergency Medicine*, vol. 14, No. 5, Suppl. 1, pp. S185-S186, Abstract 474 (May 2007).

Harrington, C.R., et al., "Senile Dementia of Lewy Body Type and Alzheimer Type Are Biochemically Distinct in Terms of Paired Helical Filaments and Hyperphosphorylated Tau Protein," *Dementia*, vol. 5, pp. 215-228 (1994).

Hashimoto, Kenji, et al., "Phencyclidine-Induced Cognitive Deficits in Mice Are Improved by Subsequent Subchronic Administration of the Novel Selective α7 Nicotinic Receptor Agonist SSR180711," *Biological Psychiatry*, vol. 63, pp. 92-97 (2008).

Hauser, T.A., et al., "TC-5619: An alpha7 neuronal nicotinic receptor-selective agonist that demonstrates efficacy in animal models of the positive and negative symptoms and cognitive dysfunction of schizophrenia," *Biochemical Pharmacology*, vol. 78, No. 7, pp. 803-812 (Oct. 1, 2009).

Haydar, Simon N., et al., "SAR and biological evaluation of SEN12333/WAY-317538: Novel alpha 7 nicotinic acetylcholine receptor agonist," *Bioorganic & Medicinal Chemistry*, vol. 17, pp. 5247-5258 (2009).

Heeschen, Christopher, et al., "A novel angiogenic pathway mediated by non-neuronal nicotinic acetylcholine receptors," *The Journal of Clinical Investigation*, vol. 110, No. 4, pp. 527-536 (Aug. 2002).

Hyde, Thomas M., et al., "Cholinergic systems and schizophrenia: primary pathology or epiphenomena?" *Journal of Chemical Neuroanatomy*, vol. 22, pp. 53-63 (2001).

Jeyarasasingam, G., et al., "Stimulation of Non-α7 Nicotinic Receptors Partially Protects Dopaminergic Neurons From 1-Methyl-4-Phenylpyridinium-Induced Toxicity in Culture," *Neuroscience*, vol. 109, No. 2, pp. 275-285 (2002).

Jin, Y., et al., "Genomic polymorphisms within alpha 7 nicotinic acetylcholine receptor and severe sepsis in Chinese Han population," *International Journal of Immunogenetics*, vol. 37, pp. 361-365 (2010).

Kotha, Sambasivarao, et al., "Recent applications of the Suzuki-Miyaura cross-coupling reaction in organic synthesis," *Tetrahedron*, vol. 58, pp. 9633-9695 (2002).

(56) References Cited

OTHER PUBLICATIONS

Kuzmin, Alexander, et al., "Effects of subunit selective nACh receptors on operant ethanol self-administration and relapse-like ethanol-drinking behavior," *Psychopharmacology*, vol. 203, pp. 99-108 (2009).

Leiser, Steven C., et al., "A cog in cognition: How the α7 nicotinic acetylcholine receptor is geared towards improving cognitive defects," *Pharmacology & Therapeutics*, vol. 122, No. 3, pp. 302-311 (Jun. 2009).

Leonard, S., et al., "Smoking and mental illness," *Pharmacology, Biochemistry and Behavior*, vol. 70, pp. 561-570 (2001).

Liu, Chong, et al., "Antishock effect of anisodamine involves a novel pathway for activating α7 nicotinic acetylcholine receptor," *Critical Care Medicine*, vol. 37, No. 2, pp. 634-641 (2009).

Manns, Joseph R., et al., "The visual paired-comparison task as a measure of declarative memory," *PNAS*, vol. 97, No. 22, pp. 12375-12379 (Oct. 24, 2000).

Mansvelder, Huibert D., et al., "Nicotinic modulation of neuronal networks: from receptors to cognition," *Psychopharmacology*, vol. 184, pp. 292-305 (2006).

Marrero, Mario B., et al., "Convergence of alpha 7 nicotinic acetylcholine receptor-activated pathways for anti-apoptosis and anti-inflammation: Central role for JAK2 activation of STAT3 and NF-κB," *Brain Research*, vol. 1256, pp. 1-7 (2009).

Martin, Laura F., et al., "Sensory Gating and Alpha-7 Nicotinic Receptor Gene Allelic Variants in Schizoaffective Disorder, Bipolar Type," *American Journal of Medical Genetics Part B: Neuropsychiatric Genetics*, vol. 144B, No. 5, pp. 611-614 (Jul. 5, 2007).

Martin, Laura F., et al., "Alpha-7 nicotinic receptor agonists: potential new candidates for the treatment of schizophrenia," *Psychopharmacology*, vol. 174, pp. 54-64 (2004).

McKay, Bruce E., et al., "Regulation of synaptic transmission of plasticity by neuronal nicotinic acetylcholine receptors," *Biochemical Pharmacology*, vol. 74, pp. 1120-1133 (2007).

Nagele, R.G., et al., "Intracellular Accumulation of β-Amyloid$_{1-42}$ in Neurons is Facilitated by the α7 Nicotinic Acetylcholine Receptor in Alzheimer's Disease," *Neuroscience*, vol. 110, No. 2, pp. 199-211 (2002).

Ng, Herman J., et al., "Nootropic α7 nicotinic receptor allosteric modulator derived from GABA$_A$ receptor modulators," *Proceedings of the National Academy of Sciences*, vol. 104, No. 19, pp. 8059-8064 (May 8, 2007).

Nizri, Eran, et al., "The Role of Cholinergic Balance Perturbation in Neurological Diseases," *Drug News & Perspectives*, vol. 20, No. 7, pp. 421-429 (Sep. 2007).

Nordberg, Agneta, et al., "Neuroprotection in Alzheimer's Disease—New Strategies for Treatment," *Neurotoxicity Research*, vol. 2, pp. 157-165 (2000).

O'Donnell, Christopher J., et al., "Discovery of 4-(5-Methyloxazolo[4,5-b]pyridine-2-yl)-1,4-diazabicyclo[3.2.2]nonane (CP-810,123), a Novel α7 Nicotinic Acetylcholine Receptor Agonist for the Treatment of Cognitive Disorders in Schizophrenia: Synthesis, SAR Development, and in Vivo Efficacy in Cognition Models," *Journal of Medicinal Chemistry*, vol. 53, pp. 1222-1237 (2010).

Olincy, Ann, et al., "Proof-of-Concept Trial of an α7 Nicotinic Agonist in Schizophrenia," *Archives of General Psychiatry*, vol. 63, pp. 630-638 (Jun. 2006).

Olincy, Ann, "Nicotine Receptor Dysfunction in Schizophrenia and Therapeutic Effects of Nicotine Agonist DMXBA," *Biological Psychiatry*, vol. 57, p. 13S, Abstract No. 44 (2005).

Paterson, David, et al., "Neuronal nicotinic receptors in the human brain," *Progress in Neurobiology*, vol. 61, pp. 75-111 (2000).

Peña, Geber, et al., "Unphosphorylated STAT3 modulates alpha7 nicotinic receptor signaling and cytokine production in sepsis," *European Journal of Immunology*, vol. 40, No. 9, pp. 2580-2589 (Sep. 2010).

Peng, ZZ, et al., "The transmission of disequilibrium analysis between neuronal nicotinic acetylcholine receptor alpha 7 subunit gene polymorphisms and schizophrenia," *Zhonghua Yi Xue Yi Chuan Xue Za Zhi*, vol. 25, No. 2, pp. 154-158 (Apr. 2008).

Perry, Elaine, et al., "Nicotinic receptor subtypes in human brain ageing, Alzheimer and Lewy body diseases," *European Journal of Pharmacology*, vol. 393, pp. 215-222 (2000).

Pfefferkorn, Jeffrey A., et al., "Design and synthesis of hepatoselective, pyrrole-based HMG-CoA reductase inhibitors" *Bioorganic & Medicinal Chemistry Letters*, vol. 17, pp. 4538-4544 (2007).

Pichat, Philippe, et al., "SSR180711, a Novel Selective α7 Nicotinic Receptor Partial Agonist: (II) Efficacy in Experimental Models Predictive of Activity Against Cognitive Symptoms of Schizophrenia," *Neuropsychopharmacology*, vol. 32, pp. 17-34 (2007).

"Product Identification Guide," *Physicians' Desk Reference*, 58th Edition, Thomson PDR, Montvale, NJ, pp. 303-340 (2004).

"Product Information—Eisai," *Physicians' Desk Reference*, 58th Edition, Thomson PDR, Montvale, NJ, pp. 1221-1223 (2004).

"Product Information—Janssen," *Physicians' Desk Reference*, 58th Edition, Thomson PDR, Montvale, NJ, pp. 1759-1764 (2004).

"Product Information—Novartis Pharmaceuticals," *Physicians' Desk Reference*, 58th Edition, Thomson PDR, Montvale, NJ, pp. 2252-2259 (2004).

"Product Information—Pfizer," *Physicians' Desk Reference*, 58th Edition, Thomson PDR, Montvale, NJ, pp. 2570-2573 (2004).

Redrobe, John P., et al., "α7 nicotinic acetylcholine receptor activation ameliorates scopolamine-induced behavioural changes in a modified continuous Y-maze task in mice," *European Journal of Pharmacology*, vol. 602, pp. 58-65 (2009).

Remingtons' Pharmaceutical Sciences, 18th Edition, p. 1445 (1990).

Roncarati, Renza, et al., "Procognitive and Neuroprotective Activity of a Novel α7 Nicotinic Acetylcholine Receptor Agonist for Treatment of Neruodegenerative and Cognitive Diseases," *The Journal of Pharmacology and Experimental Therapeutics*, vol. 329, No. 2, pp. 459-468 (2009).

Rosas-Ballina, M., et al., "Cholinergic control of inflammation," *Journal of Internal Medicine*, vol. 265, pp. 663-679 (2009).

Rosas-Ballina, Mauricio, et al., "The Selective α7 Agonist GTS-21 Attenuates Cytokine Production in Human Whole Blood and Human Monocytes Activated by Ligands for TLR2, TLR3, TLR4, TLR9, and RAGE," *Molecular Medicine*, vol. 15, No. 7-8, pp. 195-202 (Jul.-Aug. 2009).

Rowbotham, Michael C., et al., "A randomized, double-blind, placebo-controlled trial evaluating the efficacy and safety of ABT-594 in patients with diabetic peripheral neuropathic pain," *Pain*, vol. 146, pp. 245-252 (2009).

Rowley, T.J., et al., "Antinociceptive and anti-inflammatory effects of choline in a mouse model of postoperative pain," *British Journal of Anaesthesia*, vol. 105, No. 2, pp. 201-207 (2010).

Rubboli, F., et al., "Distribution of Neuronal Nicotinic Receptor Subunits in Human Brain," *Neurochemistry International*, vol. 25, No. 1, pp. 69-71 (1994).

Sanberg, Paul R., et al., "Nicotine for the Treatment of Tourette's Syndrome," *Pharmacology & Therapeutics*, vol. 74, No. 1, pp. 21-25 (1997).

Schröder, Nils, et al., "High-Yielding, Versatile, and Practical [Rh(III)Cp]-Catalyzed *Ortho* Bromination and Iodination of Arenes," *Journal of the American Chemical Society*, vol. 134, pp. 8298-8301 (2012).

Schuller, Hildegard M., et al., "Interaction of tobacco-specific toxicants with the neuronal α$_7$ nicotinic acetylcholine receptor and its associated mitogenic signal transduction pathway: potential role in lung carcinogenesis and pediatric lung disorders," *European Journal of Pharmacology*, vol. 393, pp. 265-277 (2000).

Solinas, Marcello, et al., "Nicotinic α$_7$ Receptors as a New Target for Treatment of Cannabis Abuse," *The Journal of Neuroscience*, vol. 27, No. 21, pp. 5615-5620 (May 23, 2007).

Stahl, P. Heinrich, et al., *Handbook of Pharmaceutical Salts: Properties, Selection, and Use*, Wiley-VCH, Weinheim, pp. 1-374 (2002).

Suemaru, K, et al., "Involvement of neuronal nicotinic receptor in psychiatric disorders," *Nihon Yakurigaku Zasshi*, vol. 119, No. 5, pp. 295-300 (May 2002).

(56) References Cited

OTHER PUBLICATIONS

Szoka, Jr., Francis, et al., "Comparative Properties and Methods of Preparation of Lipid Vesicles (Liposomes)," *Annual Review of Biophysics & Bioengineering*, vol. 9, pp. 467-508 (1980).

Taguchi, Kazuhiko, et al., "Synthesis of quinolines from amino alcohol and ketones catalyzed by [IrCl(cod)]$_2$ or IrCl$_3$ under solvent-free conditions," *Tetrahedron Letters*, vol. 46, pp. 4539-4542 (2005).

Thomsen, Morten S., et al., "Cognitive Improvement by Activation of $\alpha_7$ Nicotinic Acetylcholine Receptors: From Animal Models to Human Pathophysiology," *Current Pharmaceutical Design*, vol. 16, pp. 323-343 (2010).

Timmermann, Daniel B., et al., "An Allosteric Modulator of the $\alpha 7$ Nicotinic Acetylcholine Receptor Possessing Cognition-Enhancing Properties in Vivo," *The Journal of Pharmacology and Experimental Therapeutics*, vol. 323, No. 1, pp. 294-307 (2007).

Trissel, Lawrence A., "Intravenous Infusion Solutions," *ASHP Handbok on Injectable Drugs*, Fourth Edition, American Society of Hospital Pharmacists, Inc., Bethesda, MD, pp. 622-630 (1986).

Tsuang, Debby W., et al., "Examination of Genetic Linkage of Chromosome 15 to Schizophrenia in a Large Veterans Affairs Cooperative Study Sample," *American Journal of Medical Genetics (Neuropsychiatric Genetics)*, vol. 105, pp. 662-668 (2001).

Van Kampen, Marja, et al., "AR-R 17779 improves social recognition in rats by activation of nicotinic $\alpha_7$ receptors," *Psychopharmacology*, vol. 172, pp. 375-383 (2004).

Verbois, S.L., et al. "Chronic nicotine treatment attenuates $\alpha 7$ nicotinic receptor deficits following traumatic brain injury," *Neuropharmacology*, vol. 44, pp. 224-233 (2003).

Wang, Hoau-Yan, et al., "Dissociating β-Amyloid from $\alpha 7$ Nicotinic Acetylcholine Receptor by a Novel Therapeutic Agent, S 24795, Normalizes $\alpha 7$ Nicotinic Acetylcholine and NMDA Receptor Function in Alzheimer's Disease Brain," *The Journal of Neuroscience*, vol. 29, No. 35, pp. 10961-10973 (Sep. 2, 2009).

Wang, Juan, et al., "Huperzine A Improves Chronic Inflammation and Cognitive Decline in Rats With Cerebral Hypoperfusion," *Journal of Neuroscience Research*, vol. 88, pp. 807-815 (2010).

Wasserman, Todd H., et al., "Clinical Comparison of the Nitrosoureas," *Cancer*, vol. 36, pp. 1258-1268 (1975).

Weiss, Robert B., et al., "A Candidate Gene Approach Identifies the *CHRNA5-A3-B4* Region as a Risk Factor for Age-Dependent Nicotine Addition," *PLoS Genetics*, vol. 4, No. 7, e1000125, pp. 1-11 (Jul. 2008).

Westman, M., et al., "Cell Specific Synovial Expression of Nicotinic Alpha 7 Acetylcholine Receptor in Rheumatoid Arthritis and Psoriatic Arthritis," *Scandinavian Journal of Immunology*, vol. 70, pp. 136-140 (2009).

Wilens, Timothy E., et al., "Neuronal Nicotinic Receptor Agonists for the Treatment of Attention-Deficit/Hyperactivity Disorder: Focus on Cognition," *Biochemical Pharmacology*, vol. 74, No. 8, pp. 1212-1223 (Oct. 15, 2007).

Yadav, J. S., et al., "Zinc-mediated acylation and sulfonation of pyrrole and its derivatives," *Tetrahedron Letters*, vol. 43, pp. 8133-8135 (2002).

Young, Jared W., et al., "Impaired attention is central to the cognitive deficits observed in alpha 7 deficient mice," *European Neuropsychopharmacology*, vol. 17, pp. 145-155 (2007).

Young, Jared W., et al., "Nicotine Improves Sustained Attention in Mice: Evidence for Involvement of the $\alpha 7$ Nicotinic Acetylcholine Receptor," *Neuropsychopharmacology*, vol. 29, pp. 891-900 (2004).

Zhao, Xilong, et al., "Post-Stroke Dementia: Nootropic Drug Modulation of Neuronal Nicotinic Acetylcholine Receptors," *Annals New York Academy of Sciences*, vol. 939, pp. 179-186 (2001).

\* cited by examiner

Figure 1: Novel Object Recognition task

Figure 2: Social Recognition task.

4-(5-(4-CHLOROPHENYL)-2-(2-CYCLOPROPYLACETYL)-1,4-DIMETHYL-1H-PYRROL-3-YL)BENZENESULFONAMIDE AS ALPHA 7 NACHR MODULATOR

CROSS-REFERENCE TO RELATED APPLICATIONS

The present application is a U.S. National Phase Patent Application of emending International Patent Application No. PCT/IB2014/061891, filed Jun. 2, 2014, which claims the benefit of Indian Provisional Patent Application No. 1937/MUM/2013, filed Jun. 3, 2013, the disclosures of which are hereby incorporated by reference in their entireties.

FIELD OF THE INVENTION

The present invention relates to 4-(5-(4-chlorophenyl)-2-(2-cyclopropylacetyl)-1,4-dimethyl-1H-pyrrol-3-yl)benzenesulfonamide (Compound 1), its tautomeric form, its pharmaceutically acceptable salts, its pharmaceutical compositions, its combination with one or more of suitable other medicaments, and its use as nicotinic acetylcholine receptor α7 subunit (α7 nAChR) modulator.

CROSS-REFERENCE TO A RELATED APPLICATION

The present application claims the benefit of Indian Provisional Patent Application No. 1937/MUM/2013 filed on Jun. 3, 2013, the disclosure of which is incorporated herein by reference in its entirety.

BACKGROUND OF THE INVENTION

Cholinergic neurotransmission, mediated primarily through the neurotransmitter acetylcholine (ACh), is a predominant regulator of the physiological functions of the body via the central and autonomic nervous system. ACh acts on the synapses of the neurons present in all of the autonomic ganglia, neuromuscular junctions, and the central nervous system. Two distinct classes of ACh target receptors viz. muscarinic (mAChRs) and the nicotinic (nAChRs) have been identified in the brain, forming a significant component of receptors carrying out its mnemonic and other vital physiological functions.

Neural nicotinic ACh receptors (NNRs) belong to the class of ligandgated ion channels (LGIC) comprising five subunits (α2-α10, β2-β4) arranged in heteropentameric (α4β2) or homopentameric (α7) configuration (David Paterson et al., Progress in Neurobiology, 61 (2000), 75-111). α4β2 and α7 nAChR constitute the predominant subtypes expressed in the mammalian brain. α7 nAChR has attained prominence as a therapeutic target due to its abundant expression in the learning and memory centres of brain, hippocampus and the cerebral cortex (F. Rubboli et al., Neurochem. Int., 1994, 25 (1), 69-71). Particularly, α7 nAChR is characterized by a high $Ca^{2+}$ ion permeability, which is responsible for neurotransmitter release and consequent modulation of excitatory and inhibitory neurotransmission (Manickavasagom Alkondon et al., European Journal of Pharmacology, 393 (2000), 59-67; Federico Dajas-Bailador et al., TRENDS in Pharmacological Sciences, 2004, 25(6), 317-324). Furthermore, high $Ca^{2+}$ ion influx also has implications on the long-term potentiation of memory via alterations in gene expression (Robert S. Bitner et al., The Journal of Neuroscience, 2007, 27(39), 10578-10587; Bruce E. McKay et al., Biochemical Pharmacology, 74 (2007), 1120-1133).

Several recent studies have confirmed the role of α7 nAChR in neural processes like attention, memory and cognition (Huibert D. Mansvelder et al., Psychopharmacology, (2006), 184, 292-305; Wai Kit Chan et al., Neuropharmacology, 52 (2007), 1641-1649; Jared W. Young et al., European Neuropsychopharmacology, (2007), 17, 145-155). Gene polymorphisms associated with the α7 nAChR protein CHRNA7 have been implicated in the genetic transmission of schizophrenia, related neurophysiological sensory gating deficits and resultant cognitive impairment (Robert Freedman et al., Biol. Psychiatry, 1995, 38, 22-33; Debby W. Tsuang et al., American Journal of Medical Genetics (Neuropsychiatric Genetics, 105, 662-668 (2001)). Also, preclinical studies in α7 nAChR knock-out and anti-sense oligonucleotide treated mice have demonstrated impaired attention and defective cognition underscoring the prominent role of α7 nAChR in cognition (Peter Curzon et al., Neuroscience Letters, 410 (2006), 15-19; Jared W. Young et al., Neuropsychopharmacology, (2004), 29, 891-900). Additionally, pharmacological blockade of α7 nAChR impairs memory and its activation enhances the same in preclinical rodent models, thereby implicating α7 nAChR as a target for cognitive enhancement (Kenji Hashimoto et al., Biol. Psychiatry, 2008, 63, 92-97).

Pathological brain function in sensory-deficit disorders has been associated with nicotinic cholinergic transmission particularly through α7 receptors (Robert Freedman et al., Biol. Psychiatry, 1995, 38, 22-33; T Debby W. Tsuang et al., American Journal of Medical Genetics (Neuropsychiatric Genetics), 105, 662-668 (2001); Robyn Carson et al., Neuromol., Med. (2008), 10, 377-384; S. Leonard et al., Pharmacology Biochemistry and Behaviour, 70 (2001), 561-570; Robert Freedman et al., Current Psychiatry Report, 2003, 5, 155-161; Tyrone D. Cannon et al., Current Opinion Psychiatry, 2005, 18, 135-140). A defective pre-attention processing of sensory information is understood to be the basis of cognitive fragmentation in schizophrenia and related neuropsychiatric disorders (Steven C. Leiser et al., Pharmacology & Therapeutics, 122(3), (2009), 302-311). Genetic linkage studies have traced sharing of the α7 gene locus for several affective, attention, anxiety and psychotic disorders (S. Leonard et al., Pharmacology, Biochemistry and Behaviour, 70 (2001), 561-570; Suemaru K. Folia et al., Folia Pharmacol. Jpn., 119, 295-300 (2002)).

Perturbations in the cholinergic and glutamatergic homeostasis have long been implicated as causative factors for a host of neurological diseases, including dementia(s) (Eran Nizri et al., Drug News Perspect., 2007, 20(7), 421-429). Dementia is a severe, progressive, multi-factorial cognitive disorder affecting memory, attention, language, and problem solving. Nicotinic ACh receptor, particularly the interaction of α7 receptor with $α\beta_{1-42}$, is implicated as an up-stream pathogenic event in Alzheimer's disease, which is a major causative factor for dementia (Hoau-Yan Wang et al., The Journal of Neuroscience, 2009, 29(35), 10961-10973). Moreover, gene polymorphisms in CHRNA7 have been implicated in dementia with Lewy bodies (DLB) and Pick's disease (Agnes Feher et al., Dement. Geriatr. Cogn. Disord., 2009, 28, 56-62).

Disease modification potential of the nAChRs, particularly the α7 receptor, has been recognized. For example, disease-modification of Alzheimer's disease (AD) and Parkinson's disease (PD) has been proposed by enhancing neuron survival and preventing neurodegeneration (Hoau- Yan Wang et al., The Journal of Neuroscience, 2009, 29(35), 10961-10973; R. G. Nagele et al., Neuroscience, 2002, 110(2), 199-211; G. Jeyarasasingam et al., Neuroscience, 2002, 109, 275-285). Additionally, it has been proposed that α7 nAChR induced activation of anti-apoptotic (BCL-2) and anti-inflammatory pathways in the brain could have neuroprotective effects in neurodegenerative diseases (Mario B. Marrero et al., Brain Research, 2009, 1256, 1-7). Dopamine-containing neurons of the ventral tegmental area (VTA) and laterodorsal tegmental nucleus (LDT) are known to express nicotinic ACh receptors, particularly the α4, α3, β2, β3, and β4 subunits (Alexander Kuzmin et al., Psychopharmacology, (2009), 203, 99-108). Nicotinic ACh receptors α4β2 and α3β4 have been identified by the candidate-gene approach to have a strong mechanistic link for nicotine addiction (Robert B. Weiss et al., PLoS Genetics, 2008, 4(7), e1000125). α7 nAChR has particularly been studied for a putative role in cannabis addiction (Marcello Solinas et al., The Journal of Neuroscience, 2007, 27(21), 5615-5620). Varenicline, a partial agonist of α4β2, has demonstrated better efficacy in reducing smoking addiction and relapse prevention than buproprion (Jon O. Ebbert et al., Patient Preference and Adherence, 2010, 4, 355-362).

The presence of a high-affinity nicotine binding site at α4β2 nAChR in the descending inhibitory pathways from the brainstem has sparked interest in the antinociceptive properties of nicotinic ACh receptor agonists like epibatidine (Michael Decker et al., Expert Opin. Investig. Drugs, (2001), 10(10), 1819-1830). Several new developments have opened the area for the use of nicotinic modulators in pain therapy (Michael C. Rowbotham et al., PAIN, 146, (2009), 245-252).

Another key role of the α7 nAChR is its ability to modulate the production of pro-inflammatory cytokines, like interleukins (IL), tumor necrosis factor alpha (TNF-α), and high mobility group box (HMGB-1) in the central nervous system. Consequently, anti-inflammatory and antinociceptive effects have been demonstrated in pain disorders (M. Imad Damaj et al., Neuropharmacology, 39 (2000), 2785-2791). Additionally, 'cholinergic anti-inflammatory pathway' has been proposed to be a regulator of local and systemic inflammation and neuro-immune interactions through neural and humoral pathways (Margot Gallowitsch-Puerta et al., Life Sci., 2007, 80(24-25), 2325-2329; Mauricio Rosas-Ballina et al., Mol. Med., 15(7-8), 195-202 (2009); M. Rosas-Ballina et al., J. Intern. Med., 2009, 265, 663-679). Selective modulators of nicotinic ACh receptors, particularly the α7type, like GTS-21, attenuate cytokine production and IL-1β after endotoxin exposure. Furthermore, α7 nAChR are understood to have a central role in arthritis pathogenesis and potential therapeutic strategy for treatment of joint inflammation (M. Westman et al., Scandinavian Journal of Immunology, 2009, 70, 136-140). A putative role for α7 nAChR has also been implicated in severe sepsis, endotoxemic shock and systemic inflammation (Y. Jin, et al., International Journal of Immunogenetics, 37, 361-365; Chong Liu et al., Crit. Care Med., 2009, 37(2), 634-641).

Angiogenesis is a critical physiological process for cell survival and is pathologically important for cancer proliferation; several non-neural nicotinic ACh receptors, particularly α7, α5, α3, β2, and β4, are involved in such processes (Hugo R. Arias et al., International Journal of Biochemistry and Cell Biology, 41 (2009), 1441-1451; Christopher Heeschen et al., The Journal of Clinical Investigation, 2002, 110(4), 527-536). The role of nicotinic ACh receptors in the development of cervical cancer, lung carcinogenesis and pediatric lung disorders in smoking-exposed population has been studied (Itzel E. Calleja-Macias et al., Int. J. Cancer., 124, 1090-1096 (2009); Hildegard M. Schuller et al., European Journal of Pharmacology, 393 (2000), 265-277). Several α7 nAChR agonists and partial agonists have been characterized for their efficacy in clinical and preclinical studies. EVP-6124, an agonist at α7 nAChR, has reportedly demonstrated a significant improvement in sensory processing and cognition biomarkers in Phase Ib study with patients suffering from schizophrenia (EnVivo Pharmaceuticals press release 2009, Jan. 12). GTS-21 (DMXB-Anabaseine), an α7 nAChR agonist, in the P II clinical trials, has reportedly shown efficacy in improving cognitive deficits in schizophrenia and the inhibition of endotoxin-induced TNF-α release (Ann Olincy et al., Biol. Psychiatry, 2005, 57(8, Suppl.), Abst 44; Ann Olincy et al., Arch. Gen. Psychiatry, 2006, 63, 630-638; Richard Goldstein et al., Acad. Emerg. Med., 2007, 14(5), s185-s186). CP-810123, an α7 nAChR agonist, reportedly exhibits protection against scopolamine-induced dementia and inhibition of amphetamine-induced auditory evoked potentials in preclinical studies (Christopher J. O'Donnell et al., J. Med. Chem., 2010, 53, 1222-1237). SSR-180711A, also an α7 nAChR agonist, reportedly enhances learning and memory, and protects against MK-801/scopolamine-induced memory loss and prepulse inhibition in preclinical studies (John P. Redrobe et al., European Journal of Pharmacology, 602 (2009), 58-65; John Dunlop et al., Journal of Pharmacology and Experimental Therapeutics, 2009, 328, 766-776; Philippe Pichat et al., Neuropsychopharmacology, 2007, 32, 17-34). SEN-12333 reportedly protects against scopolamine-induced amnesia in a passive avoidance test in preclinical studies (Renza Roncarati et al., The Journal of Pharmacology and Experimental Therapeutics, 2009, 329, 459-468). AR-R-17779, an agonist of the α7 nAChR, reportedly exhibits an improvement in the social recognition task performed in rats (Marja Van Kampen et al., Psychopharmacology, 2004, 172, 375-383). ABBF, an agonist of the α7 nAChR, reportedly improves social recognition memory and working memory in the Morris maze task in rats (Frank G. Boess et al., The Journal of Pharmacology and Experimental Therapeutics, 2007, 321, 716-725). TC-5619, a selective α7 nAChR agonist has reportedly demonstrated efficacy in animal models of positive and negative symptoms and cognitive dysfunction in schizophrenia (T. A. Hauser et al., Biochemical Pharmacology, 78 (2009), 803-812).

An alternative strategy to reinforce or potentiate the endogenous cholinergic neurotransmission of ACh without directly stimulating the target receptor is the positive allosteric modulation (PAM) of α7 nAChR (E. X. Albuquerque et al., Alzheimer Diseases and Associated Disorder, Vol. 15, Suppl 1, S19-S25). Several PAMs have been characterized, albeit only in preclinical stages of discovery. A-86774, an α7 nAChR PAM, reportedly improves sensory gating in DBA/2 mice by significantly reducing the T: C ratio in a preclinical model of schizophrenia (Ramin Faghih et al., Journal of Medicinal Chemistry, 2009, 52, 3377-3384). XY-4083, an α7 nAChR PAM, reportedly normalizes the sensorimotor gating deficits in the DBA/2 mice and memory acquisition in the 8-arm radial maze test without altering the receptor desensitization kinetics (Herman J. Hg et al., PNAS, 2007, 104 (19), 8059-8064). Yet another PAM, PNU-120596, reportedly alters α7 nAChR desensitization kinetics while simultaneously protecting against the disruption of prepulse inhibition by MK-801. NS-1738, another PAM, reportedly exhibits efficacy in-vivo in the animal models of social recognition and spatial memory acquisition in the Morris maze task (Daniel B. Timmermann et al., Journal of Pharmacology and Experimental Therapeutics, 2007, 323, 294-307). In addition, several patents/applications published are listed below—US 2006/0142349, US 2007/0142450, US 2009/0253691, WO 2007/031440, WO 2009/115547, WO2009/135944, WO 2009/127678, WO 2009/127679, WO 2009/043780, WO2009/043784, U.S. Pat. No. 7,683,084, U.S. Pat. No. 7,741,364, WO 2009/145996, US 2010/0240707, WO 2011/064288, US 2010/0222398, US 2010/0227869, EP 1866314, WO 2010/130768, WO 2011/036167, US 2010/0190819, WO 2012/104782, WO 2012/114285, WO 2012/131576, WO 2013/005153, and WO 2013/132380, which reportedly disclose efficacy of allosteric modulators of nicotinic ACh receptors, underscoring their therapeutic potential.

Despite the foregoing proposals in the art, there exists a need for novel modulators of the nicotinic acetylcholine receptors, particularly the α7 nAChR, pharmaceutical compositions comprising such modulators, and methods of treating diseases, disorders, or conditions that are treatable or preventable by the use of such modulators.

BRIEF SUMMARY OF THE INVENTION

The present invention provides 4-(5-(4-chlorophenyl)-2-(2-cyclopropylacetyl)-1,4-dimethyl-1H-pyrrol-3-yl)benzenesulfonamide, its tautomeric form, its pharmaceutically acceptable salts, its pharmaceutical compositions, its combinations with one or more of suitable other medicaments, and its use as nicotinic acetylcholine receptor α7 subunit (α7 nAChR) modulator.

Thus the present invention further provides a pharmaceutical composition containing 4-(5-(4-chlorophenyl)-2-(2-cyclopropylacetyl)-1,4-dimethyl-1H-pyrrol-3-yl)benzenesulfonamide, its tautomeric form, and/or its pharmaceutically acceptable salts in combination with pharmaceutically acceptable carriers, diluents, and the like, which is useful for the treatment and/or prophylaxis of diseases, disorders, or conditions such as Alzheimer's disease (AD), mild cognitive impairment (MCI), senile dementia, vascular dementia, dementia of Parkinson's disease, attention deficit disorder, attention deficit hyperactivity disorder (ADHD), dementia associated with Lewy bodies, AIDS dementia complex (ADC), Pick's disease, dementia associated with Down's syndrome, Huntington's disease, cognitive deficits associated with traumatic brain injury (TBI), cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts and lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

The present invention also provides a pharmaceutical composition containing 4-(5-(4-chlorophenyl)-2-(2-cyclopropylacetyl)-1,4-dimethyl-1H-pyrrol-3-yl)benzenesulfonamide, its tautomeric form, its pharmaceutically acceptable salts, in combination with pharmaceutically acceptable carriers, diluents, and the like, which is useful for the treatment and/or prophylaxis of diseases, disorders, or conditions classified or diagnosed as major or minor neurocognitive disorders, or disorders arising due to neurodegeneration.

The present invention also provides a method of treatment wherein 4-(5-(4-chlorophenyl)-2-(2-cyclopropylacetyl)-1,4-dimethyl-1H-pyrrol-3-yl)benzenesulfonamide, its tautomeric form, or its pharmaceutically acceptable salt is administered in combination with or as adjunct to medications used in the treatment of attention deficit hyperactivity disorders, schizophrenia, and other cognitive disorders such as Alzheimer's disease, Parkinson's dementia, vascular dementia or dementia associated with Lewy bodies, or traumatic brain injury.

The present invention also provides a method of treatment wherein 4-(5-(4-chlorophenyl)-2-(2-cyclopropylacetyl)-1,4-dimethyl-1H-pyrrol-3-yl)benzenesulfonamide, its tautomeric form, or its pharmaceutically acceptable salt is administered in combination with or as an adjunct to acetylcholinesterase inhibitors, disease modifying drugs or biologics for neurodegenerative disorders, dopaminergic drugs, antidepressants, or a typical or atypical antipsychotic.

The present invention also provides the use of 4-(5-(4-chlorophenyl)-2-(2-cyclopropylacetyl)-1,4-dimethyl-1H-pyrrol-3-yl)benzenesulfonamide, its tautomeric form, or its pharmaceutically acceptable salt, in the preparation of a medicament for treating a disease, disorder, or condition selected from the group of disorders classified or diagnosed as major or minor neurocognitive disorders and disorders arising due to neurodegeneration.

The present invention also provides the use of 4-(5-(4-chlorophenyl)-2-(2-cyclopropylacetyl)-1,4-dimethyl-1H-pyrrol-3-yl)benzenesulfonamide, its tautomeric form, or its pharmaceutically acceptable salt, in the preparation of a medicament for treating a disease, disorder, or condition selected from attention deficit hyperactivity disorders, schizophrenia, cognitive disorders, Alzheimer's disease, Parkinson's dementia, vascular dementia or dementia associated with Lewy bodies, and traumatic brain injury.

The present invention also provides the use of 4-(5-(4-chlorophenyl)-2-(2-cyclopropylacetyl)-1,4-dimethyl-1H-pyrrol-3-yl)benzenesulfonamide, its tautomeric form, or its pharmaceutically acceptable salt, in combination with or as an adjunct to acetylcholinesterase inhibitors, disease modifying drugs or biologics for neurodegenerative disorders, dopaminergic drugs, antidepressants, or a typical or atypical antipsychotic.

BRIEF DESCRIPTION OF THE SEVERAL VIEWS OF THE DRAWINGS

FIG. 1A depicts the result obtained using Compound 1 in 24 h time delay-induced amnesia. Subchronic (7 day) treatment with compound 1 (0.05 mg/Kg, p.o.) significantly increased the discrimination index as compared to vehicle-treated group. FIG. 1B depicts the result obtained using Compound 1 in Scopolamine-induced amnesia. Subchronic (7 day) treatment with compound 1(0.05 mg/Kg, p.o.) significantly increased the discrimination index as compared to scopolamine treated group.

FIG. 2A depicts the result obtained using Compound 1 in 24 h time delay-induced amnesia. Subchronic (7 day) treatment with compound 1 (0.05 mg/Kg, p.o.) significantly decreased the recognition index (RI) as compared to vehicle-treated group. FIG. 2B depicts the result obtained using Compound 1 in Scopolamine-induced amnesia. Subchronic (7 day) treatment with compound 1 (0.05 mg/Kg, p.o.) significantly decreased the recognition index (RI) as compared to scopolamine treated group.

DETAILED DESCRIPTION OF THE INVENTION

The present invention provides 4-(5-(4-chlorophenyl)-2-(2-cyclopropylacetyl)-1,4-dimethyl-1H-pyrrol-3-yl)benzenesulfonamide, its tautomeric form, its pharmaceutically acceptable salts, its combinations with suitable other medicaments, and its pharmaceutical compositions.

According to another aspect of the present invention, 4-(5-(4-chlorophenyl)-2-(2-cyclopropylacetyl)-1,4-dimethyl-1H-pyrrol-3-yl)benzenesulfonamide was prepared by methods outlined in Scheme—1 below. However, the synthetic methods should not be construed limiting the invention; compound 1 may also be prepared by any method known to those skilled in the art.

reaction conditions as described in J. S. Yadav et al., Tetrahedron Letters, 2002, 43, 8133-8135, yields (3). Preferably, the reaction is carried out in toluene in the presence of zinc.

Bromination of (3) using a brominating reagent such as bromine, N-bromosuccinimide, or phosphorous tribromide (as described in Elena Dvornikova et al., Synlett, 2002, No. 7, 1152-1154) yields 1-(3-bromo-5-(4-chlorophenyl)-1,4-dimethyl-1H-pyrrol-2-yl)-2-cyclopropylethanone (4). Preferably, the bromination reaction is carried out in the presence of N-bromosuccinimide in THF.

Suzuki coupling of (4) with (4-sulfamoylphenyl)boronic acid (5), which is available commercially, provides 4-(5-(4-chlorophenyl)-2-(2-cyclopropylacetyl)-1,4-dimethyl-1H-pyrrol-3-yl)benzenesulfonamide (Compound 1). Suzuki coupling with boronic acid can be carried out following the procedures well known in the art (Sambasivarao Kotha et. al., Tetrahedron, 2002, 58, 9633-9695; Timothy E, Bander et al. J. Am. Chem. Soc., 2005, 127, 4685-4696). Preferably, the Suzuki coupling is carried out in a mixture of ethanol and Scheme-1

Scheme—1 shows a method of preparation of 4-(5-(4-chlorophenyl)-2(2-cyclopropylacetyl)-1,4-dimethyl-1H-pyrrol-3-yl)benzenesulfonamide (1) from 2-(4-chlorophenyl)-1,3-dimethyl-1H-pyrrole (2) in accordance with an embodiment of the invention.

Kazuhiko Taguchi et al., Tetrahedron Letters, 2005, 46, 4539-4542 teach a method for the preparation of (2).

Reaction of (2) with 2-cyclopropyl-N,N-dimethylacetamide, in the presence of POCl$_3$ under Vilsmeier-Haackreaction conditions as described in Jeffrey A. Pfefferkorn et al., Tetrahedron, 2007, 63, 8124-8134, yields 1-(5-(4-chlorophenyl)-1,4-dimethyl-1H-pyrrol-2-yl)-2-cyclopropylethanone (3).

Alternatively, reaction of (2) with 2-cyclopropylacetyl chloride, in the presence of acid or zinc under Friedel-Crafts toluene, in the presence of a base such as potassium phosphate, potassium carbonate or the like, and tetrakis(triphenylphosphine)palladium(0) at a temperature of about 50° C. or higher.

The term 'room temperature' denotes any temperature ranging between about 20° C. to about 40° C., except and otherwise it is specifically mentioned in the specification.

The intermediates and the compound of the present invention may obtained in pure form in a manner known per se, for example, by distilling off the solvent in vacuum and re-crystallizing the residue obtained from a suitable solvent, such as pentane, diethyl ether, isopropyl ether, chloroform, dichloromethane, ethyl acetate, acetone or their combinations or subjecting them to one of the purification methods, such as column chromatography (e.g., flash chromatography) on a suitable support material such as alumina or silica gel using an eluent such as dichloromethane, ethyl acetate, hexane, methanol, acetone and their combinations. Preparative LC-MS method is also used for the purification of the molecules described herein.

Salts of 4-(5-(4-chlorophenyl)-2-(2-cyclopropylacetyl)-1, 4-dimethyl-1H-pyrrol-3-yl)benzenesulfonamide can be obtained by dissolving it in a suitable solvent, for example in a chlorinated hydrocarbon, such as methylene chloride or chloroform or a low molecular weight aliphatic alcohol, for example, ethanol or isopropanol, which is then treated with the desired acid or base as described by Stephen M. Berge, et al., "Pharmaceutical Salts," a review article in Journal of Pharmaceutical sciences, 1977, 66(1), 1-19, and in the Handbook of Pharmaceutical Salts, Properties, Selection, and Use, by P. Heinrich Stahl and Camille G. Wermuth, Wiley-VCH (2002). Lists of suitable salts can also be found in Remington's Pharmaceutical Sciences, 18$^{th}$ ed., Mack Publishing Company, Easton, Pa., 1990, p. 1445, and Stephen M. Berge et al., Journal of Pharmaceutical Science, 1977, 66(1), 1-19. For example, they can be a salt of an alkali metal (e.g., sodium or potassium), alkaline earth metal (e.g., calcium), or an ammonium salt.

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The prodrugs can be prepared in situ during the isolation and purification of the compound, or by separately reacting the purified compound with a suitable derivatizing agent. For example, the hydroxy group of a tautomeric form can be converted into esters via treatment with a carboxylic acid in the presence of a catalyst. Examples of cleavable alcohol prodrug moieties include substituted- or unsubstituted-, branched or unbranched lower alkyl ester moieties, e.g., ethyl esters, lower alkenyl esters, di-lower alkylamino lower-alkyl esters, e.g., dimethylaminoethyl ester, acylamino lower alkyl esters, acyloxy lower alkyl esters (e.g., pivaloyloxymethyl ester), aryl esters, e.g., phenyl ester, aryl-lower alkyl esters, e.g., benzyl ester, optionally substituted, e.g., with methyl, halo, or methoxy substituents aryl and aryl-lower alkyl esters, amides, lower-alkyl amides, di-lower alkyl amides, and hydroxy amides.

The present invention further provides a pharmaceutical composition comprising a compound as described above and a pharmaceutically acceptable carrier. The present invention provides a pharmaceutical composition comprising a pharmaceutically acceptable carrier and an effective amount, e.g., a therapeutically effective amount, including a prophylactically effective amount of the aforesaid compound, or a salt thereof, of the present invention.

The pharmaceutically acceptable carrier can be any of those conventionally used and is limited only by chemico-physical considerations, such as solubility and lack of reactivity with the compound, and by the route of administration. The pharmaceutically acceptable carriers described herein, for example, vehicles, adjuvants, excipients, or diluents, are well known to those who are skilled in the art and are readily available to the public.

The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavour, usually sucrose and acacia or tragacanth, as well as pastilles comprising the active ingredient in an inert base, such as gelatin and glycerine, or sucrose and acacia, emulsions, gels, and the like containing, in addition to the active ingredient, such carriers as are known in the art.

The compound, a salt thereof, or a tautomer thereof, can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol, polyethylene glycol, or glycerol, ketals, such as 2,2-dimethyl-1, 3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (e) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compound of the present invention, salt thereof, or a tautomer thereof, may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4$^{th}$ ed., pages 622-630 (1986).

Additionally, the compound of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

In accordance with the invention, modulation of the nicotinic cholinergic receptors, particularly α7, provides for efficacy in a range of cognitive states, right from pre-attention to attention and subsequently working, reference and recognition memory. Accordingly, the present invention finds application in the treatment and prophylaxis of a multitude of diseases or conditions including, either one or combinations of, schizophrenia, schizophreniform disorder, cognitive deficits in schizophrenia, brief psychotic disorder, delusional disorder, schizoaffective disorder, shared psychotic disorder, paranoid personality disorder, schizoid personality disorder, schizotypal personality disorder, attention deficit disorder, attention deficit hyperactivity disorder, depression, maniac depression, major depressive disorder, posttraumatic stress disorder, generalized anxiety disorder, tourette's syndrome, cyclothymic disorder, dysthymic disorder, agoraphobia, panic disorder (with or without agoraphobia), phobias (including social phobia) and bipolar disorders (Morten S. Thomsen, et al., Current Pharmaceutical Design, 2010, 16, 323-343; Peng Zhi-Zhen et al., Zhonghua Yi Xue Yi Chuan Xue Za Zhi, 2008, 25, 154-158; Jared W. Young, et al., European Neuropsychopharmacology, (2007), 17, 145-155; Laura F. Martin, et al., American Journal of Medical Genetics, Part B (Neuropsychiatric Genetics), 2007, 144B, 611-614; Laura F. Martin, et al., Psychopharmacology, (2004), 174, 54-64; Agnes Feher, et al., Dement. Geriatr. Cogn. Disord., 2009, 28, 56-62; Timothy E. Wilens, et al., Biochem. Pharmacol., 2007, 74(8), 1212-1223; S. L. Verbois, et al., Neuropharmacology, 44 (2003), 224-233; Paul R. Sanberg, et al., Pharmacol. Ther., 1997, 74(1), 21-25). The cholinergic system, particularly through α7 nAChR, also has implications in traumatic brain injury-induced psychosis. Accordingly, the present invention also finds application in the treatment of deficits in cholinergic α7 nAChR following traumatic brain injury.

Modulation of nicotinic ACh receptors, particularly the α7 subtype, also helps to supplement the down-regulated cholinergic receptor expression and transmission as in dementia(s), and also in slowing disease progression by reduction of the α7-αβ$_{1-42}$ complexation and internalization in AD and Down's syndrome (Agneta Nordberg, et al., Neurotoxicity Research, 2000, 2, 157-165; Simon N. Haydar et al., Bioorganic & Medicinal Chemistry, 17 (2009), 5247-5258; Stephen I. Deutsch et al., Clinical Neuropharmacology, 2003, 26(5), 277-283).

The compound of the invention, a salt thereof, or a tautomer thereof, also finds application in the treatment and prophylaxis of a number of diseases or conditions including, either one or combinations of, dementia(s) due to Alzheimer's disease, dementia with Lewy bodies, or dementia due to Down's syndrome, head trauma, stroke, hypoperfusion, Parkinson's disease, Huntington's disease, Prion diseases, progressive supranuclear palsy, radiation therapy, brain tumors, normal-pressure hydrocephalus, subdural hematoma, human immunodeficiency virus (HIV) infection, vitamin deficiency, hypothyroidism, chronic medication, drug abuse, drug addiction, alcohol abuse, alcohol addiction, metal poisoning such as aluminium, lead, mercury, heavy metal etc., syphilis, Lyme disease, viral encephalitis, fungal infection and cryptococcosis (Xilong Zhao et al., Annals New York Academic Science, 2001, 939, 179-186; Elaine Perry et al., European Journal of Pharmacology, 393 (2000), 215-222; C. R. Harrington et al., Dementia, 1994, 5, 215-228; Juan Wang et al., Journal of Neuroscience Research, 88, 807-815 (2010); Kamil Duris et al., Stroke, 2011, 42(12), 3530-3536). The compound of the present invention also finds application in the prophylaxis and preventive measures immediately after early-stage identification of neurodegenerative disease such as Alzheimer's disease and Parkinson's disease.

Modulation of the nicotinic ACh receptors, particularly the α4β2, α3β4 and α7 receptors, also has implications in the development of therapies for nicotine or cannabis addiction and relapse prevention. Accordingly, the compound of the invention finds application in the prophylaxis or therapy of nicotine addiction, cannabis addiction, and relapse prevention of nicotine or cannabis addiction. Additionally, the invention further provides an alternative therapy for non-responding addiction patients, patients having intolerable side-effects with de-addiction therapies or those requiring long-term maintenance therapies. (Alexander Kuzmin et al., Psychopharmacology, (2009), 203, 99-108; Robert B. Weiss et al., PLoS Genetics, 2008, 4(7), e1000125; Marcello Solinas et al., The Journal of Neuroscience, 2007, 27(21), 5615-5620; Jon O Ebbert et al., Patient Preference and Adherence, 2010, 4, 355-362).

The efficacy of the compound of the invention in treating the above diseases, disorders, or conditions can be determined by any suitable method. For example, the Novel Object Recognition Task (NORT) is the preclinical equivalent of the visual paired comparison task in humans, a sensitive screen for evaluation of memory dysfunctions related to cognitive impairments associated with schizophrenia (CIAS), dementia and other amnesic states (Manns, J. R. et al., Proc. Natl. Acad. Sci. U.S.A., 2000, 97, 12375-12379). Novelty recognition and discrimination forms the core principle for preclinical tests mimicking human amnesic conditions, with underpinnings to critical brain structures including the hippocampus and the cerebral cortex (Clark, R. E. et al., J. Neurosci., 2000, 20, 8853-8860). NORT is based on the innate tendency of the rodents to explore novelty in an otherwise familiar environment, a dependent measure for the formation and retention of memory episodes. It has successfully been utilized as a rapid, single-trial assay for investigating effects of pharmacological manipulations on memory and attentional parameters in rodents (Ennaceur A et al., Behav. Brain. Res., 2010, 215, 244-254). Both the procognitive effects per se and the reversal of chemically-induced disruption of memory can reliably be evaluated on the short-term, intermediate and long-term formation of episodic memory through NORT. Typically, with this task, modulation of a single-memory episode is recorded as it is more vulnerable to loss rather than being reinforced by multiple presentations, and hence adding more sensitivity to measurement. Retention interval of 1 h is commonly utilized in combination of amnesic drugs like scopolamine or MK-801 or PCP, when mimicking memory loss in specific disease conditionssuch as dementias or schizophrenia. For time-delay induced natural forgetting, intervals of 24 h or more are preferred.

Social functioning requires intact processing of the emotional conditioned and un-conditioned stimuli based on the formation of short-term recognition or working memory, which is hypothesized to be deregulated in several neuropsychiatric disorders such as Alzheimer's disease, Schizophrenia and Parkinson's disease (Dickerson F. et al., Schizophr. Res., 1996, 21, 75-83). Particularly, patients with schizophrenia are poor in initiation and maintenance of social interactions due to deficits in short-term memory and cholinergic neurotransmission (Hyde T. M. et al., J. Chem. Neuroanat., 2001, 22, 53-63). Recognition cues for these short-term memories are thought to have a strong 'olfactory' component, the neural substrates of which have been traced to the perirhinal and entorhinal cortices in parahippocampal region. Role played by hippocampus and basolateral amygdala has also been well documented in formation of recognition memory (Dantzer R. et al., Behav. Brain Res. 1990, 40, 53-60). Short-term working/recognition memory can be rapidly evaluated in the rat social recognition task for several targets using pharmacological modulation. Both the procognitive potential per se and the anti-amnesic properties (reversal of scopolamine and MK-801-induced memory deficits) can be reliably tested for the compound of the invention using this model.

The compound, a tautomer thereof, or salt thereof of the invention also finds application in the treatment and prophylaxis of a number of pain conditions including, either one or combinations of, pain arising from, peripheral nervous system (PNS), post-diabetic neuralgia (PDN), post-herpetic neuralgia (PHN), multiple sclerosis, Parkinson's disease, low-back pain, fibromyalgia, post-operative pain, acute pain, chronic pain, mononeuropathy, primary lateral sclerosis, pseudobulbar palsy, progressive muscular palsy, progressive bulbar palsy, postpolio syndrome, diabetes induced polyneuropathy, acute demyelinating polyneuropathy (Guillain-Barre syndrome), acute spinal muscular atrophy (Werdnig-Hoffman disease) and secondary neurodegeneration (Diana L. Donnelly-Roberts et al., Journal of Pharmacology and Experimental Therapeutics, 1998, 285, 777-786; T. J. Rowley et al., British Journal of Anaesthesia, 105(2), 201-207, (2010); A. Bruchfeld et al., Journal of Internal Medicine, 2010, 268, 94-101).

The compound, tautomer thereof, or salt thereof of the invention also finds application in the treatment and prophylaxis of a number of inflammation and pain related states involving TNF-$\alpha$ and in providing symptomatic relief in either any one or combination of, rheumatoid arthritis, bone resorption diseases, atherosclerosis, inflammatory bowel disease, Crohn's disease, inflammation, cancer pain, muscle degeneration, osteoarthritis, osteoporosis, ulcerative colitis, rhinitis, pancreatitis, spondylitis, acute respiratory distress syndrome (ARDS), joint inflammation, anaphylaxis, ischemia reperfusion injury, multiple sclerosis, cerebral malaria, septic shock, tissue rejection of graft, brain trauma, toxic shock syndrome, herpes virus infection (HSV-1 & HSV-2), herpes zoster infection, sepsis, fever, myalgias, asthma, uveititis, contact dermatitis, obesity-related diseases, and endotoxemia (Ida A. J. Giebelen et al., Shock, 2007, 27(4), 443-447; Pena Geber et al., Eur. J. Immunol., 2010, 40, 2580-2589).

The present invention further provides a pharmaceutical composition, containing compound 1, a tautomer thereof, or a pharmaceutically acceptable salt thereof, in combination with a pharmaceutically acceptable carrier, excipient, diluents, or the like.

The pharmaceutically acceptable carrier (or excipient) is preferably one that is chemically inert to the compound of the invention and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Such compositions include solutions containing anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Topical formulations, including those that are useful for transdermal drug release, are well known to those of skill in the art and are suitable in the context of the present invention for application to skin.

A compound of the present invention, alone or in combination with other suitable components, can be made into aerosol formulations to be administered via inhalation. A compound of the invention is preferably supplied in finely divided form along with a surfactant and propellant. Typical percentages of the compound of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

The concentration of the compound in the pharmaceutical formulations can vary, e.g., from less than about 1% to about 10%, to as much as 20% to 50% or more by weight, and can be selected primarily by fluid volumes, and viscosities, in accordance with the particular mode of administration selected.

For example, a typical pharmaceutical composition for intravenous infusion could be made up to contain 250 ml of sterile Ringer's solution, and 100 mg of the compound of the invention. Actual methods for preparing parenterally administrable composition of the invention will be known or apparent to those skilled in the art and are described in more detail in, for example, *Remington's Pharmaceutical Science* (17$^{th}$ ed., Mack Publishing Company, Easton, Pa., 1985).

It will be appreciated by one of ordinary skill in the art that, in addition to the afore-described pharmaceutical compositions, the compound of the invention can be formulated as inclusion complexes, such as cyclodextrin inclusion complexes, or liposomes. Liposomes can serve to target a compound of the invention to a particular tissue. Liposomes can also be used to increase the half-life of a compound of the invention. Many methods are available for preparing liposomes, as described in, for example, Szoka et al., Ann. Rev. Biophys. Bioeng., 1980, 9, 467, and U.S. Pat. No. 4,235,871, U.S. Pat. No. 4,501,728, U.S. Pat. No. 4,837,028, and U.S. Pat. No. 5,019,369.

In another embodiment, the pharmaceutical compositions are useful for the treatment and/or prophylaxis of diseases, disorders or conditions classified or diagnosed as major or minor neurocognitive disorders, or disorders arising due to neurodegeneration.

The present invention also provides a method of administering 4-(5-(4-chlorophenyl)-2-(2-cyclopropylacetyl)-1,4-dimethyl-1H-pyrrol-3-yl) benzenesulfonamide or a pharmaceutically acceptable salt thereof in combination with or as adjunct to medications used in the treatment of attention deficit hyperactivity disorders, schizophrenia, and other cognitive disorders such as Alzheimer's disease, Parkinson's dementia, vascular dementia or dementia associated with Lewy bodies, and/or traumatic brain injury.

The present invention also provides a method of administering 4-(5-(4-chlorophenyl)-2-(2-cyclopropylacetyl)-1,4-dimethyl-1H-pyrrol-3-yl) benzenesulfonamide, a tautomer thereof, or a pharmaceutically acceptable salt thereof in combination with or as an adjunct to acetylcholinesterase inhibitors, disease modifying drugs or biologics for neurodegenerative disorders, dopaminergic drugs, antidepressants, and/or typical or an atypical antipsychotic.

Accordingly, 4-(5-(4-chlorophenyl)-2-(2-cyclopropylacetyl)-1,4-dimethyl-1H-pyrrol-3-yl) benzenesulfonamide or its pharmaceutically acceptable salts are useful for preventing or treating a disorder mediated by nicotinic acetylcholine receptors. The compound, a tautomer, or salt thereof, can be administered to a subject having such a disorder or susceptible to such disorders in a therapeutically effective amount. 4-(5-(4-chlorophenyl)-2-(2-cyclopropylacetyl)-1,4-dimethyl-1H-pyrrol-3-yl) benzenesulfonamide or its pharmaceutically acceptable salts are particularly useful for a method of treating a mammal having a condition where modulation of the nicotinic acetylcholine receptor activity is of therapeutic benefit, wherein the method is accomplished by administering a therapeutically effective amount of the compound of the present invention to a subject having, or susceptible to, such a disorder.

The compound a tautomer, or salt thereof, of the invention can be administered in a dose sufficient to treat the disease, condition or disorder. Such doses are known in the art (see, for example, the Physicians' Desk Reference(2004)). The compound a tautomer, or salt thereof, can be administered using techniques such as those described in, for example, Wasserman et al., Cancer, 1975, 36, 1258-1268, and Physicians' Desk Reference, 58$^{th}$ ed., Thomson P D R (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 µg to about 50 mg of the compound of the invention per kg body weight of the individual. For a 70 kg patient, dosages of from about 10 µg to about 200 mg of the compound of the invention would be more commonly used, depending on a patient's physiological response.

By way of example and not intending to limit the invention, the dose of the compound, a tautomer, or salt thereof, described herein for methods of treating or preventing a disease or condition as described above can be about 0.001 to about 1 mg/kg body weight of the subject per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for the described methods can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

In accordance with embodiments, the present invention provides methods of treating, preventing, ameliorating, and/or inhibiting a condition modulated by the nicotinic acetylcholine receptor comprising administering compound 1, a tautomer thereof, or a salt thereof.

The invention also provides a method of preventing or treating a disease or its symptoms or a disorder mediated partially or completely by nicotinic acetylcholine receptors, said method comprising administering to a subject having or susceptible to said disease or its symptoms or disorder with a therapeutically effective amount of 4-(5-(4-chlorophenyl)-2-(2-cyclopropylacetyl)-1,4-dimethyl-1H-pyrrol-3-yl)benzenesulfonamide, its tautomeric form, or its pharmaceutically acceptable salts.

The disorder, condition, and disease as described above are selected from Alzheimer's disease, mild cognitive impairment, senile dementia, vascular dementia, dementia of Parkinson's disease, attention deficit disorder, attention deficit hyperactivity disorder, dementia associated with Lewy bodies, AIDS dementia complex, Picks disease, dementia associated with Down's syndrome, Huntington's disease, cognitive deficits associated with traumatic brain injury, cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts, lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

The disease, disorder and condition as described above are particularly selected from the group classified or diagnosed as major or minor neurocognitive disorders, or disorders arising due to neurodegeneration.

The invention further provides a method comprising administering 4-(5-(4-chlorophenyl)-2-(2-cyclopropylacetyl)-1,4-dimethyl-1H-pyrrol-3-yl)benzenesulfonamide in combination with or as adjunct to medications utilized in the treatment of attention deficit hyperactivity disorders, schizophrenia, cognitive disorders such as Alzheimer's disease, Parkinson's dementia, vascular dementia or dementia associated with Lewy bodies, or traumatic brain injury. The medications can be administered simultaneously, sequentially, or cyclically with 4-(5-(4-chlorophenyl)-2-(2-cyclopropylacetyl)-1,4-dimethyl-1H-pyrrol-3-yl)benzenesulfonamide.

The invention further provides a method comprising administering 4-(5-(4-chlorophenyl)-2-(2-cyclopropylacetyl)-1,4-dimethyl-1H-pyrrol-3-yl)benzenesulfonamide in combination with or as an adjunct to other medications, for example, acetylcholinesterase inhibitors, disease modifying drugs or biologics for neurodegenerative disorders, dopaminergic drugs, antidepressants, or a typical or atypical antipsychotic. The other medications can be administered simultaneously, sequentially, or cyclically with 4-(5-(4-chlorophenyl)-2-(2-cyclopropylacetyl)-1,4-dimethyl-1H-pyrrol-3-yl)benzenesulfonamide.

The invention also provides for the use of 4-(5-(4-chlorophenyl)-2-(2-cyclopropylacetyl)-1,4-dimethyl-1H-pyrrol-3-yl)benzenesulfonamide, its tautomeric form, and its pharmaceutically acceptable salts in the preparation of a medicament for preventing or treating a disease or its symptoms or a disorder mediated partially or completely by nicotinic acetylcholine receptors.

In the use described above, the disease or disorder or condition is selected from the group classified or diagnosed as major or minor neurocognitive disorders, or disorders arising due to neurodegeneration.

The use described above is in combination with or as adjunct to medications utilized in the treatment of attention deficit hyperactivity disorders, schizophrenia, cognitive disorders, Alzheimer's disease, Parkinson's dementia, vascular dementia or dementia associated with Lewy bodies, and traumatic brain injury.

The use described above is in combination with or as an adjunct to acetylcholinesterase inhibitors, disease modifying drugs or biologics for neurodegenerative disorders, dopaminergic drugs, antidepressants, or a typical or atypical antipsychotic.

It would be useful to list here some of the known medications that are used to treat attention deficit hyperactivity disorders, schizophrenia, cognitive disorders, Alzheimer's disease, Parkinson's dementia, vascular dementia or dementia associated with Lewy bodies, and traumatic brain injury and acetylcholinesterase inhibitors, disease modifying drugs or biologics for neurodegenerative disorders, dopaminergic drugs, antidepressants, or a typical or atypical antipsychotic.

The terms "treat" or "prevent," as well as words stemming therefrom, as used herein, do not necessarily imply 100% or complete treatment or prevention. Rather, there are varying degrees of treatment and prevention of which one of ordinary skill in the art recognizes as having a potential benefit or therapeutic effect. In this respect, the inventive methods can provide any amount of any level of treatment or prevention of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment or prevention provided by the inventive method can include treatment or prevention of one or more conditions or symptoms of the disorder. Also, for purposes herein, "treatment" or "prevention," can encompass delaying the onset of the disorder, or a symptom or condition thereof.

In accordance with the invention, the term subject includes an "animal" which in turn includes a mammal such as, without limitation, the order Rodentia, such as mice, and the order Lagomorpha, such as rabbits. It is preferred that the mammals are from the order Carnivora, including Felines (cats) and Canines (dogs). It is more preferred that the mammals are from the order Artiodactyla, including Bovines (cows) and Swine (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In accordance with the invention, 'Minimal/Minimum effective dose' is the smallest dose that produces a desired therapeutic outcome. In case of behavioral studies, it is the minimum dose that produced statistically significant ($p<0.05$, 95% confidence interval) behavioral outcome in comparison to the control-treated group. In case of delay-dependent control is vehicle-treated group, and scopolamine group is the comparative control in scopolamine-induced amnesia experiments.

Following are the abbreviations used and meaning thereof in the specification:

AIDS: Acquired Immunodeficiency Syndrome.

HBSS: Hanks Balanced Salt Solution.

HEPES: 4-(2-hydroxyethyl)piperazine-1-ethanesulfonic acid.

THF: Tetrahydrofuran.

TLC: Thin Layer Chromatography.

NMR: Nuclear Magnetic Resonance.

α7 nAChR: nicotinic acetylcholine receptor α7 subunit.

The following examples further illustrate the present invention and should not be construed in any way to limit the scope of the present invention.

All $^1$H NMR spectra were determined in the solvents indicated and chemical shifts are reported in δ units downfield from the internal standard tetramethylsilane (TMS) and interproton coupling constants are reported in Hertz (Hz).

Preparative Example

Preparation of 4-(5-(4-chlorophenyl)-1,4-dimethyl-2-propionyl-1H-pyrrol-3-yl)benzenesulfonamide (Compound A)

Compound A was prepared according to the procedures described in Examples 10 and 11 of WO 2012/114285.

Example 1

Preparation of 4-(5-(4-chlorophenyl)-2-(2-cyclopropylacetyl)-1,4-dimethyl-1H-pyrrol-3-yl)benzenesulfonamide (Compound 1)

Step 1: Preparation of 1-(5-(4-chlorophenyl)-1,4-dimethyl-1H-pyrrol-2-yl)-2-cyclopropylethanone (3) using 2-cyclopropyl-N,N-dimethylacetamide POCl$_3$ (1.36 g, 0.82 ml, 8.88 mmol) was added to 2-cyclopropyl-N,N-dimethylacetamide (prepared according to the procedure described in Nils SchrOder et al., J. Am. Chem. Soc., 2012, 134, 8298-8301), 1.13 g (8.88 mmol) at 0° C. and under stirring and the reaction was continued at 0° C. for 15 min. The reaction mixture was allowed to warm up to room temperature, stirred for 20 min, and diluted with 1,2-dichloroethane (10 ml). 2-(4-chlorophenyl)-1,3-dimethyl-1H-pyrrole (prepared according to the procedure described in Kazuhiko Taguchi et. al., Tetrahedron Letters, 2005, 46, 4539-4542) (1.64 g, 8.0 mmol) was dissolved in 1,2-dichloroethane (20 ml) and was added to the reaction mixture at 0° C. The reaction mixture was heated to reflux temperature (95° C.) for 30 min. The progress of the reaction was monitored TLC. The reaction mixture was cooled to room temperature. Sodium acetate (4.01 g, 48.9 mmol) was dissolved in water (15 ml) and added to the reaction mixture. The reaction mixture was stirred at 100° C. for 1 hr. The progress of the reaction was monitored by TLC. The reaction mixture was cooled to room temperature, diluted with DCM (50 ml) and water (20 ml) was added to it. The organic layers were separated, dried over anhydrous sodium sulfate, filtered and concentrated to obtain a crude product. This crude product was purified by column chromatography using 5-10% ethyl acetate in hexanes as an eluent to obtain the title compound 3(0.77 g, 30.5%). MS: m/z 288 (M+1).

$^1$H NMR (CDCl$_3$, 400 MHz): δ 7.47 (d, J=8.8 Hz, 2H), 7.23 (d, J=8.8 Hz, 2H), 6.84 (s, 1H), 3.79 (s, 3H), 2.68 (d, J=6.8 Hz, 2H), 2.02 (s, 3H), 1.15-1.19 (m, 1H), 0.56-0.61 (m, 2H), 0.21-0.24 (m, 2H).

Step 1: Preparation of 1-(5-(4-chlorophenyl)-1,4-dimethyl-1H-pyrrol-2-yl)-2-cyclopropylethanone (3) using 2-cyclopropylacetyl chloride 2-cyclopropylacetyl chloride (11.83 g, 100.00 mmol) solution in chlorobenzene (60 ml) was added to the stirred solution of 2-(4-chlorophenyl)-1,3-dimethyl-1H-pyrrole (prepared according to the procedure given in Kazuhiko Taguchi et al., Tetrahedron Letters, 2005, 46, 4539-4542) (17.10 g, 83.00 mmol) and Zinc (10.87 g, 166.00 mmol) in toluene (100 ml) at 25° C. The reaction mixture was stirred at 25° C. for 3 h. The progress of the reaction was monitored by TLC. The mixture was diluted with a saturated solution of sodium bicarbonate (100 ml) and the layers were separated. The aqueous layer was extracted with ethyl acetate (3×100 ml). The combined organic layer was washed with water (1×50 ml) and dried over anhydrous Na$_2$SO$_4$. The solvent was evaporated under reduced pressure to obtain a crude product. The crude product was purified by column chromatography using 5-10% ethyl acetate in hexanes as an eluent to obtain the title compound 3(7.20 g, 30.1%). MS: m/z 288 (M+1).

$^1$HNMR (CDCl$_3$, 400 MHz): δ 7.47 (d, J=8.8 Hz, 2H), 7.23 (d, J=8.8 Hz, 2H), 6.84 (s, 1H), 3.79 (s, 3H), 2.68 (d, J=6.8 Hz, 2H), 2.02 (s, 3H), 1.15-1.19 (m, 1H), 0.56-0.61 (m, 2H), 0.21-0.24 (m, 2H).

Step 2: Preparation of 1-(3-bromo-5-(4-chlorophenyl)-1,4-dimethyl-1H-pyrrol-2-yl)-2-cyclopropylethanone (4)

To a stirred solution of 1-(5-(4-chlorophenyl)-1,4-dimethyl-1H-pyrrol-2-yl)-2-cyclopropylethanone (Step 1)(0.30 g, 1.04 mmol) in THF (10 ml) at −78° C. was added a solution of N-bromosuccinimide (0.18 g, 1.04 mmol) in THF (10.0 ml) in a drop wise manner. The resulting mixture was stirred at −78° C. for 10 min. The progress of the reaction was monitored by TLC. The reaction mixture was quenched by the addition of a saturated sodium bicarbonate solution (5 ml). The solvent was evaporated under reduced pressure and the residue was dissolved in ethyl acetate (30 ml). The organic layer was washed with a saturated sodium bicarbonate solution (1×10 ml) followed by water (1×10 ml). The combined organic layer was dried over anhydrous Na$_2$SO$_4$. The solvent was evaporated under reduced pressure to obtain a crude product which was purified by column chromatography using 10% ethyl acetate in hexanes to obtain the title compound 4(0.34 g, 89.0%). MS: m/z 367 (M+1).

$^1$HNMR (CDCl$_3$, 400 MHz): δ 7.48 (d, J=8.8 Hz, 2H), 7.23 (d, J=8.8 Hz, 2H), 3.71 (s, 3H), 3.03 (d, J=6.8 Hz, 2H), 1.98 (s, 3H), 1.17-1.22 (m, 1H), 0.57-0.62 (m, 2H), 0.21-0.24 (m, 2H).

Step 3: Preparation of 4-(5-(4-chlorophenyl)-2-(2-cyclopropylacetyl)-1,4-dimethyl-1H-pyrrol-3-yl)benzenesulfonamide (Compound 1)

4-aminosulfonylbenzene boronic acid (5) (0.18 g, 0.88 mmol) and potassium carbonate (0.31 g, 2.21 mmol) were added to the solution of 1-(3-bromo-5-(4-chlorophenyl)-1,4-dimethyl-1H-pyrrol-2-yl)-2-cyclopropylethanone (Step-2)(0.32 g, 0.88 mmol) in a mixture of toluene:ethanol (4:16 ml) in a tube at 25° C. Nitrogen gas was bubbled through the resulting mixture for 15 minutes. Tetrakis(triphenylphosphine)palladium(0) (0.051 g, 0.044 mmol) was added to the reaction mixture under nitrogen atmosphere and the tube was sealed. The reaction mixture was heated at 90-95° C. for 5 hr under stirring. The progress of the reaction was monitored by TLC. The reaction mixture was cooled to 25° C. and filtered through celite. The residue was washed with a mixture of 10% methanol in dichloromethane. The filtrate was concentrated under reduced pressure to obtain a crude product which was purified by column chromatography using 30% ethyl acetate in hexanes as an eluent to obtain the title compound 1 (0.12 g, 31.8%). MS: m/z 443 (M+1).

$^1$HNMR (CDCl$_3$, 400 MHz): δ 8.01 (d, J=8.4 Hz, 2H), 7.44-7.50 (m, 4H), 7.31 (d, J=8.4 Hz, 2H), 4.93 (bs-exchanges with D$_2$O, 2H), 3.72 (s, 3H), 2.09 (d, J=7.2 Hz, 2H), 1.76 (s, 3H), 0.89-0.93 (m, 1H), 0.41-0.44 (m, 2H), −0.13t to −0.11 (m, 2H).

Example 2

In Vitro Activity

Compound 1 and compound A were tested in a cell-based real-time kinetic assay in human IMR-32 cells with native expression of α7nAChR. The increase in intracellular Ca$^{2+}$ levels was measured in a Fluorometric Imaging Plate Reader (FLIPR). Test compounds and their agonist solutions were made in an assay buffer (HBSS, pH 7.4, 20 mM HEPES, and 10 mM CaCl$_2$). Briefly, cells were plated into Poly-D-Lysine coated back-walled clear-bottom 96-well microplates at a density of 80,000 to 100,000 cells/well and incubated at 37° C./5% CO$_2$ for 40-48 h prior to the experiment. For the evaluation of compound mediated potentiation of agonist response, growth media was removed from the wells and 200 μl of FLIPR calcium 4 dye (Molecular Devices) reconstituted in assay, buffer was added to the wells. After dye loading, microplates were incubated for 30 min at 37° C. and 30 min at room temperature and then directly transferred to the FLIPR. The baseline fluorescence was monitored for the first 10 to 30 second followed by the addition of 25 μl of the test compound solutions and subsequent monitoring of fluorescence changes for up to 10 min. This was followed by the addition of 25 μl of agonist solution (PNU-282987, 10 μM) and measurement of fluorescence for 4 min. (Faghih R. et al., J. Med. Chem., 2009, 52, 3377-84.)

The compound induced fold increase in agonist response (fold PAM activity) was computed by dividing the maximum effect (Max-Min fluorescence) obtained with the test compound in the presence of agonist with the agonist-alone effect. EC$_{50}$ of compound 1 and compound A were calculated using GraphPad Prism software version 5.0, by plotting compound concentrations against fold PAM activity.

Compounds 1 and A exhibited more than 15 fold PAM activity at 1 μM concentration.

Example 3

In Vivo Activity (i) Novel Object Recognition Task

Briefly, Wistar rats were acclimatized to the CNS-Laboratory-animal holding room for at least 7 days prior to the randomization, under standard housing conditions. Animals were handled and familiarized with the injection procedures during this period. Two days before the experimentation (acquisition trial, T1), rats were randomized in different treatment-groups based on their body weights namely, vehicle (Tween 80 (1%, v/v), Vitamin E TPGS (Speziol®, 10%, v/v) q.s. 100% v/v in milli-Q water, 2 ml/kg, p.o.), scopolamine (1 mg/kg, i.p.) and test compounds (Compound 1: ranging from 0.005 to 0.05 mg/kg, p.o. and compound A:ranging from 0.05 to 0.5 mg/kg, p.o.)

Vehicle or test compounds (Compounds 1 and A) were administered in a single-dose, subchronically for 7 days, and 1 h before the acquisition trial on day-8 in respective treatment-groups. In order to induce cognitive deficits, scopolamine (1 mg/kg) was injected 25 min before the acquisition trial (T1). Acquisition (T1) and Retention (T2) trials were separated by an intertrial interval of 30 min. In the first trial (acquisition trial, T1), the rats were subjected to arena with two identical objects for a period of 5 min and exploration time towards individual object was measured. In retention trial, one of the identical object was replaced with novel object.

In the time-delay induced amnesia paradigm, vehicle or test compounds (Compounds 1 and A) were administered once-daily for 7 days, and 1 h before the acquisition trial (T1) on day-8 in the respective treatment-groups. After this, a second, retention (T2) trial, was conducted on day-9. A 24 h inter-trial interval served to induce spontaneous decay of memory and resultant amnesia in this paradigm.

In the second trial (retention trial, T2), one of the objects presented in T1 was replaced by a novel object, and the rats were left to explore in the arena for 5 min. The time spent exploring the familiar (F) and the novel object (N) was recorded separately. All the animals underwent habituation session of 10 min duration 24 h prior to acquisition trial to get them acclimatized to the test arena. Both the trials (acquisition and retention) were of 5 min duration. The NOR task was performed in the square-open-field boxes (40 cm long×40 cm wide×40 cm high) made up of non-reflective PVC sheets with black surrounding walls and light gray floor. Colored plastic and glass bottles of different size, shapes and texture, served as object of exploration.

Object exploration was measured as the 'time spent by the animal' directing its nose at a distance 2 cm to the object or touching and exploring it. Time spent climbing on the object was not accounted as object exploration. In order to avoid the presence of olfactory trails, the test boxes and objects were always thoroughly cleaned between trials of individual animals.

Mean and standard error of the mean (S.E.M.) was calculated for the exploration time of each identical objects in T1, novel and familiar objects in T2 and discrimination index across the treatment groups. Exploration time within groups was compared with Student's paired t-test. Discrimination index was compared between groups by One-way ANOVA with Dunnett's post hoc test in comparison to the scopolamine-treated group or vehicle-treated group as per the paradigm. Discrimination index was compared between groups by unpaired t-test in comparison to the vehicle-treated group. $p<0.05$ was considered as significant. All statistical comparisons were performed using GraphPad Prism version 5.00 for Windows, GraphPad Software, San Diego Calif. USA.

The discrimination index (DI) was calculated based on explorations in T2 trial, using the formula.

Discrimination Index equals (time spent investigating novel object−time spent investigating familiar object)/(time spent investigating novel object+time spent investigating familiar object). Any subjects that failed to explore either of the objects during T1 and T2 were excluded from the analysis. All the experimental recordings were carried out by manual observation of animals by trained scientists. Observers were kept blind to the treatment groups.

Figure 1:
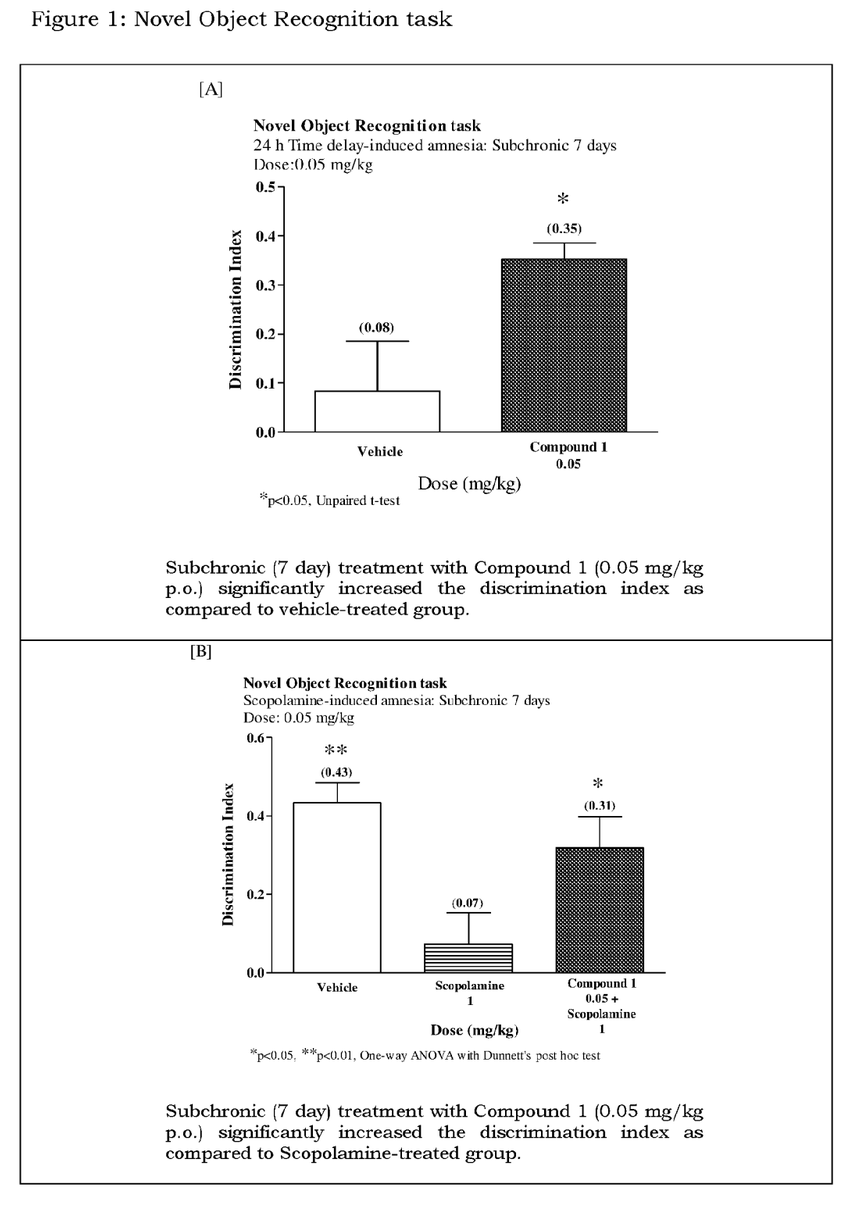
FIG. 1 depicts the results of Novel Object Recognition Task subchronic study.

Results are provided in FIG. 1.

Table 1 below shows test results of Novel Object Recognition Task (Subchronic studies) of compounds 1 and A.

TABLE 1

| Sr. No. | Study | Minimum effective dose (mg/kg) | |
|---|---|---|---|
| | | Compound 1 | Compound A |
| 1. | Scopolamine induced amnesia | 0.015 | >0.5 |
| 2. | Time-delay induced amnesia | 0.015 | 0.15 |

(ii) Social Recognition Task

Briefly, Sprague Dawley rats were acclimatized to the CNS-Laboratory-animal holding room for at least 7 days prior to the randomization, under standard housing conditions. The animals were handled and familiarized with the injection procedures during this period. Two days before the experimentation (social interaction trial, SIT1), the rats were randomized in different treatment-groups based on their body weights namely, vehicle (Tween 80 (1%, v/v), Vitamin E TPGS (Speziol®, 10%, v/v) q.s. 100% v/v in milli-Q water; 2 ml/kg, p.o.), scopolamine (0.5 mg/kg, i.p.) and test compound (Compound 1:ranging from 0.05 to 0.50 mg/kg, p.o.).

Seven days before experiment, the vehicle or the test compound was administered to the adult rats once-daily and 1 h before the SIT1 on day-8 in respective treatment-groups. Scopolamine or vehicle was administered 20 min prior to the first social interaction (acquisition, SIT1) trial; scopolamine administration served to induced amnesia. After this treatment, the animals were subjected to the first social interaction (acquisition, SIT1) trial, which was followed by a second (retention, SIT2) trial, 30 min later.

In the case of time-delay induced amnesia paradigm, the vehicle or the test compounds (Compound 1) were administered to the adult rats once-daily for 7 days and 1 h before the SIT1 on day-8, in respective treatment-groups. After this treatment, the animals were subjected to a second (retention, SIT2) trial on day-9. The 24 h inter-trial interval served to induce spontaneous decay of memory and resultant amnesia.

Both the trials (acquisition and retention) were of 5 min duration. The social recognition task was performed in the home-cages made up of transparent polycarbonate. Juvenile rats of 3-4 weeks of age served as subjects for exploration to the adult rats. Adult rats were habituated to the home-cage (without juvenile) for 5 min just before SIT1.

Subject exploration (towards juvenile) was measured as the 'time spent by the adult animal' exploring the juvenile rat socially viz. sniffing, following, climbing over or going under or aggression. In order to avoid the confounding olfactory trails, the home-cage was individualized for each adult rat. During the second trial (retention trial, SIT2), adult rats were re-exposed to the same juvenile rat previously introduced earlier in the SIT1. The time of exploration in seconds was recorded for both sessions (SIT1 and SIT2).

Mean and standard error of mean (S.E.M) were determined for the exploration time of each social recognition trial (SIT1, SIT2) and recognition index across the treatment-groups. Recognition index was compared between groups by One-way ANOVA with Dunnett's post hoc test in comparison to the scopolamine-treated group or vehicle-treated group as per paradigm. Exploration time within treatment groups was compared with unpaired student's t-test. Recognition index was compared between groups by unpaired t-test in comparison to the vehicle-treated group. $p<0.05$ was considered as significant. All statistical comparisons were performed using GraphPad Prism version 5.00 for Windows, GraphPad Software, San Diego Calif. USA.

The recognition index (RI) was calculated using the formula:

Recognition index equals(time spent investigating juvenile rat in SIT2/time spent investigating juvenile rat in SIT1).

Any subjects that failed to explore either of the objects during SIT1 and SIT2 were excluded from the analysis. All the experimental recordings were carried out by manual observation of animals by trained scientists. Observers were kept blind to the treatment groups.

Figure 2:
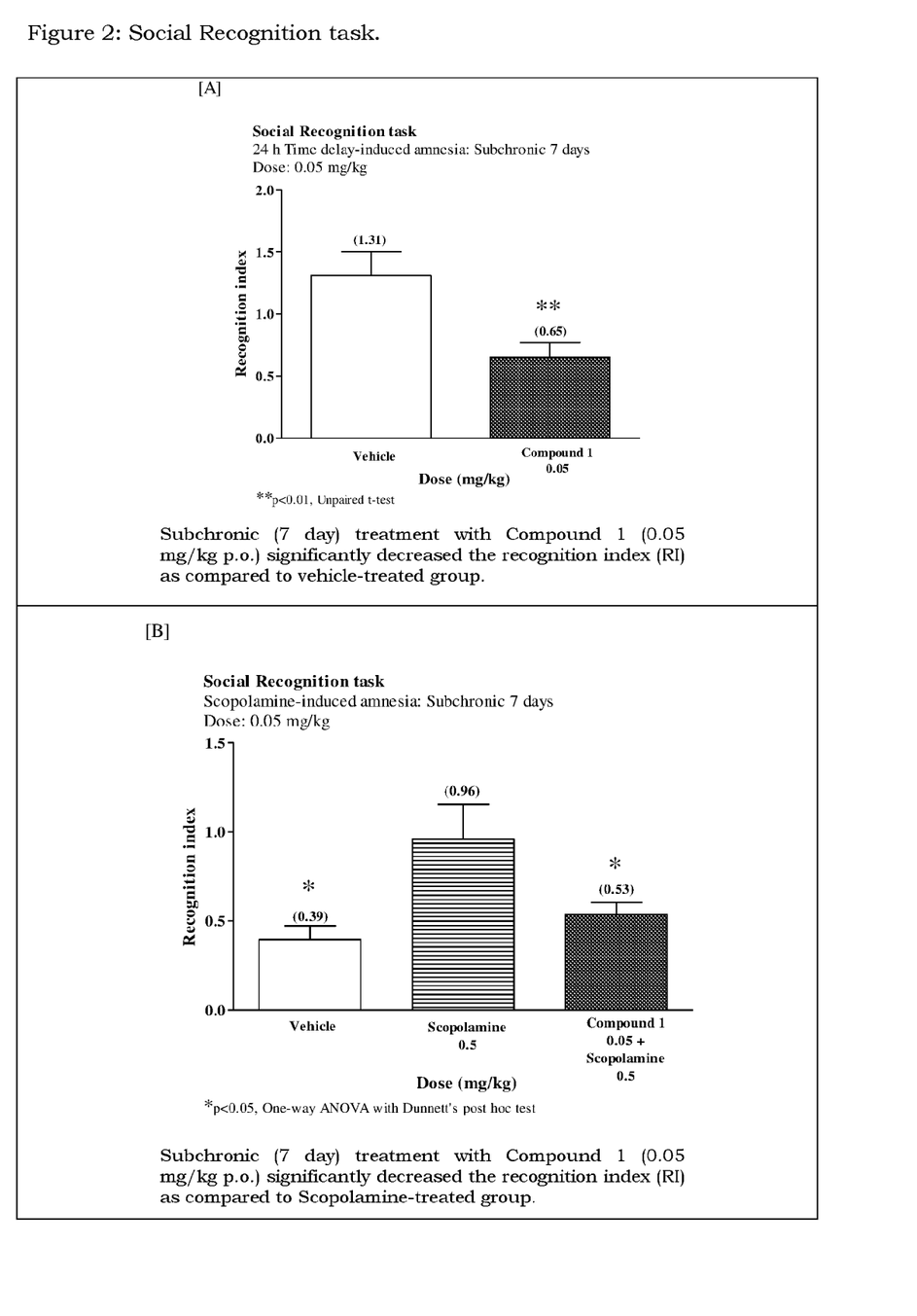
FIG. 2 depicts the results of Social Recognition Task subchronic study.

The results obtained are provided in FIG. 2.

Table 2 below shows the test results of Social Recognition Task (Subchronic study) of compound 1.

TABLE 2

| Sr. No. | Parameter | Minimum effective dose (mg/kg) of Compound 1 |
|---|---|---|
| 1. | Scopolamine induced amnesia | 0.015 |
| 2. | Time-delay induced amnesia | 0.05 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. 4-(5-(4-chlorophenyl)-2-(2-cyclopropylacetyl)-1,4-dimethyl-1H-pyrrol-3-yl)benzenesulfonamide, a tautomer thereof, or a pharmaceutically acceptable salt thereof.

2. A pharmaceutical composition comprising 4-(5-(4-chlorophenyl)-2-(2-cyclopropylacetyl)-1,4-dimethyl-1H-pyrrol-3-yl)benzenesulfonamide, a tautomer thereof, or a pharmaceutically acceptable salt thereof and a pharmaceutically acceptable carrier.

3. A method of treating a disease or its symptoms, condition, or a disorder mediated partially or completely by nicotinic acetylcholine receptors, said method comprising administering to a subject having said disease or its symptoms or disorder a therapeutically effective amount of 4-(5-(4-chlorophenyl)-2-(2-cyclopropylacetyl)-1,4-dimethyl-1H-pyrrol-3-yl)benzenesulfonamide, a tautomer thereof, or a pharmaceutically acceptable salt thereof, wherein the disorder, condition or disease is selected from the group consisting of Alzheimer's disease, mild cognitive impairment, senile dementia, vascular dementia, dementia of Parkinson's disease, attention deficit disorder, attention deficit hyperactivity disorder, dementia associated with Lewy bodies, AIDS dementia complex, Pick's disease, dementia associated with Down's syndrome, Huntington's disease, cognitive deficits associated with traumatic brain injury, cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts, lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

4. The method of claim 3, comprising administering 4-(5-(4-chlorophenyl)-2-(2-cyclopropylacetyl)-1,4-dimethyl-1H-pyrrol-3-yl)benzenesulfonamide, a tautomer thereof, or a pharmaceutically acceptable salt thereof in combination with or as adjunct to a medication utilized in the treatment of attention deficit hyperactivity disorders, schizophrenia, a cognitive disorders, or traumatic brain injury.

5. The method of claim 3, further comprising administering an acetylcholinesterase inhibitor, a disease modifying drug or biologic for treating a neurodegenerative disorder, a dopaminergic drug, an antidepressant, or a typical or an atypical antipsychotic.

6. The method of claim 4, wherein said cognitive disorder is selected from the group consisting of Alzheimer's disease, Parkinson's disease, vascular dementia and dementia associated with Lewy bodies.

* * * * *